(12) United States Patent
Nishi

(10) Patent No.: US 11,365,419 B2
(45) Date of Patent: Jun. 21, 2022

(54) HOST CELL AND METHOD FOR PRODUCING TARGET PROTEIN USING SAME

(71) Applicant: KANEKA CORPORATION, Osaka (JP)

(72) Inventor: Teruyuki Nishi, Hyogo (JP)

(73) Assignee: KANEKA CORPORATION, Osaka (JP)

( * ) Notice: Subject to any disclaimer, the term of this patent is extended or adjusted under 35 U.S.C. 154(b) by 293 days.

(21) Appl. No.: 16/441,424

(22) Filed: Jun. 14, 2019

(65) Prior Publication Data

US 2019/0300889 A1 Oct. 3, 2019

Related U.S. Application Data

(63) Continuation of application No. PCT/JP2017/044806, filed on Dec. 14, 2017.

(30) Foreign Application Priority Data

Dec. 15, 2016 (JP) .............................. JP2016-243198

(51) Int. Cl.
| | |
|---|---|
| C12N 15/81 | (2006.01) |
| C12N 5/10 | (2006.01) |
| C12N 15/09 | (2006.01) |
| C12P 21/00 | (2006.01) |

(52) U.S. Cl.
CPC ............. *C12N 15/815* (2013.01); *C12N 5/10* (2013.01); *C12N 15/09* (2013.01); *C12P 21/00* (2013.01)

(58) Field of Classification Search
None
See application file for complete search history.

(56) References Cited

U.S. PATENT DOCUMENTS

| | | | |
|---|---|---|---|
| 2011/0236942 A1* | 9/2011 | Hawkins .............. | C12N 9/0006 435/160 |
| 2015/0056675 A1 | 2/2015 | Muramatsu et al. | |
| 2015/0259710 A1 | 9/2015 | Dundon et al. | |

FOREIGN PATENT DOCUMENTS

| | | |
|---|---|---|
| EP | 2669375 A1 | 12/2013 |
| WO | 2010135678 A1 | 11/2010 |
| WO | 2012102171 A1 | 8/2012 |
| WO | 2013129393 A1 | 9/2013 |

OTHER PUBLICATIONS

Jeffries, T.W. 2006 Current Opinion in Biotechnology 17: 320-326. (Year: 2006).*
UniProtKB F2R0E4 Pichia pastoris magnesium-activated aldehyde dehydrogenase ALD6-1 2011 (5 pages). (Year: 2011).*
Yadav, V.G., et al. 2012 Metabolic Engineering 14: 233-241. (Year: 2012).*
Gerngross, T.U. 2004 Nature Biotechnology 22(11): 1409-1414. (Year: 2004).*
J.L. Cereghino et al., "Heterologous protein expression in the methylotrophic yeast *Pichia pastoris*," FEMS Microbiology Reviews, 2000, vol. 24, pp. 45-66 (22 pages).
V. Chiruvolu et al., "Recombinant protein production in an alcohol oxidase-defective strain of Pichia Pastoris in fedbatch fermentations," Enzyme and Microbial Technology, 1997, vol. 21, 277-283 (7 pages).
F.W. Krainer et al., "Recombinant protein expression in Pichia pastoris strains with an engineered methanol utilization pathway," Microbial Cell Factories, 2012, vol. 11, No. 22 (14 pages).
T. Charoenrat et al., "Enhancement of thermostable β-glucosidase Production in a Slow Methanol Utilization Strain of Pichia pastoris by Optimization of the Specific Methanol Supply Rate," Biotechnology and Bioprocess Engineering, 2015, vol. 20, pp. 315-323 (9 pages).
International Search Report issued in corresponding International Application No. PCT/JP2017/044806; dated Mar. 20, 2018 (6 pages).
Written Opinion of the International Searching Authority issued in corresponding International Application No. PCT/JP2017/044806; dated Mar. 20, 2018 (5 pages).
Extended European Search Report issued in corresponding European Application No. 17881876.1; dated May 27, 2020 (7 pages).
Marco Sonderegger et al., "Metabolic Engineering of a Phosphoketolase Pathway for Pentose Catabolism in *Saccharomyces cerevisiae*," Applied and Environmental Microbiology, May 2004, pp. 2892-2897 (6 pages).
Inan et al., "Non-Repressing Carbon Sources for Alcohol Oxidase (AOX1) Promoter of Pichia pastoris,"; Journal of Bioscience and Bioengineering, vol. 92, No. 6, pp. 585-589 (2001) (5 pages).
Eliasson et al., "Anaerobic Xylose Fermentation by Recombinant *Saccharomyces cerevisiae* Carrying XYL1, XYL2, XKS1, in Mineral Medium Chemostat Cultures"; Applied and Environmental Microbiology, vol. 66, No. 8, pp. 3381-3386 (2000) (6 pages).
Tomita et al., "Genome and Transcriptome Analysis of the Food-Yeast *Candida utilis*"; PLoS One, vol. 7, Issue 5, pp. 1-10, e37226 (May 2012) (10 pages).

* cited by examiner

*Primary Examiner* — Marsha Tsay
(74) *Attorney, Agent, or Firm* — Osha Bergman Watanabe & Burton LLP

(57) ABSTRACT

A host cell includes an inactivated gene. The inactivated gene may be a gene including the nucleotide sequence of SEQ ID NO: 34, a gene including a nucleotide sequence of a nucleic acid hybridizing under a stringent condition to a nucleic acid consisting of a nucleotide sequence complementary to the nucleotide sequence of SEQ ID NO: 34, a gene comprising a nucleotide sequence having a sequence identity of 85% or more to the nucleotide sequence of SEQ ID NO: 34, or a gene encoding an amino acid sequence having a sequence identity of 85% or more to the amino acid sequence of SEQ ID NO: 33.

7 Claims, No Drawings

Specification includes a Sequence Listing.

HOST CELL AND METHOD FOR PRODUCING TARGET PROTEIN USING SAME

TECHNICAL FIELD

One or more embodiments of the present invention relate to a novel host cell, the ability to utilize methanol of which is reduced by inactivating a specific gene, a novel host cell with improved productivity of a target protein, a vector for inactivating the aforementioned gene, and a method for producing a target protein, using the aforementioned novel host cell.

BACKGROUND

Genetic recombination has been broadly used for the production of industrially useful biomaterials, such as antibodies, enzymes, and cytokines that are utilized in medicinal and diagnostic purposes. Examples of a host used to produce a target protein according to genetic recombination include animals such as chickens, animal cells such as CHO, insects such as silkworms, insect cells such as sf9, and microorganisms such as yeasts, *Escherichia coli* and Actinomycetes. Among host organisms, yeast is advantageous in that a target protein can be produced at a low cost, because the yeast can be cultured at a large scale and at a high density in an inexpensive medium, in that purifying a target protein produced by the yeast is easy when a signal peptide is used for secretion and expression of the target protein in a culture supernatant, and in that the yeast is a eukaryote and it is possible to carry out post-translational modification such as sugar chain addition. Thus, various studies for using yeasts as a host have been conducted. An innovative technique of producing various target proteins from yeasts that can improve productivity of the target proteins drastically and enhance their cost competitiveness is desired. Such an innovative technique could be applicable to a broad range of industrial field.

One species of yeast, *Komagataella pastoris*, is a methanol-utilizing (Mut$^+$) yeast, which is excellent in terms of protein-expressing ability and can utilize an inexpensive carbon source that is advantageous in terms of industrial production. For example, Non Patent Literature 1 reports a method for producing heterologous proteins. such as a green fluorescent protein, human serum albumin, a hepatitis B virus surface antigen, human insulin and a single-chain antibody. by *Komagataella pastoris*. In order to improve the productivity of heterologous proteins by yeast, various attempts have been made, such as addition of a signal sequence, utilization of a strong promoter, codon modification, co-expression of a chaperone gene, co-expression of a transcriptional factor gene, inactivation of a protease gene derived from a host yeast, and optimization of culture conditions. For example, Patent Literature 1 reports expressing a transcriptional factor for activating a methanol-inducible promoter in *Komagataella pastoris* to improve its productivity of heterologous proteins.

By the way, production of a target protein using methanol as a carbo source in a large-scale and high-density culture system causes various problems. The problems include safety risk caused by increasing the size of a methanol storage tank, stress on cells or cell death caused by hydrogen peroxide generated as a result of oxidation of methanol, generation of heat by combustion of methanol, the supply of a large amount of oxygen for maintaining a high-density culture. In order to solve these problems, for example, Non Patent Literatures 2 to 4 disclose a method for producing a target protein by using a strain with a reduced ability to utilize methanol (Mut$^S$) caused by disruption of AOX1 gene.

CITATION LIST

Patent Literature

Patent Literature 1: International Publication No. WO 2012/102171

Non Patent Literature

Non Patent Literature 1: FEMS Microbiology Reviews 24 (2000) 45-66.
Non Patent Literature 2: Enzyme and Microbial Technology 21 (1997) 277-283.
Non Patent Literature 3: Microbial Cell Factories (2012) 11:22.
Non Patent Literature 4: Biotechnology and Bioprocess Engineering (2015) 20: 315-323.

However, producing a target protein by the strain with a reduced ability to utilize methanol (Mut$^S$) disclosed in Non Patent Literatures 2 to 4 causes novel problems such as a prolonged culture time, depletion of a carbon source, and decomposition of a target protein by protease.

SUMMARY

One or more embodiments of the present invention provide a novel means for reducing methanol utilization and improving the productivity of a target protein.

The present inventors have identified a novel protein by comprehensively analyzing the nucleotide sequence of the chromosomal DNA of a yeast belonging to the genus *Komagataella*. Then, the present inventors have found that inactivating a gene encoding the novel protein in a host cell leads to reduction of the ability to utilize methanol of the host cell. Moreover, the present inventors have also found that the inactivating of the gene improves the productivity of a target protein, and further that expressing a transcriptional factor activating a methanol-inducible promoter at a high level further improves the productivity of the target protein.

One or more embodiments of the present invention include the following aspects.

(1) A host cell, wherein any one of the following genes (a) to (d) is inactivated:
  (a) a gene comprising a nucleotide sequence as set forth in SEQ ID NO: 34,
  (b) a gene comprising a nucleotide sequence of a nucleic acid hybridizing under a stringent condition to a nucleic acid consisting of a nucleotide sequence complementary to the nucleotide sequence as set forth in SEQ ID NO: 34,
  (c) a gene comprising a nucleotide sequence having a sequence identity of 85% or more to the nucleotide sequence as set forth in SEQ ID NO: 34, and
  (d) a gene encoding an amino acid sequence having a sequence identity of 85% or more to an amino acid sequence as set forth in SEQ ID NO: 33.
(2) The host cell according to the above (1), which is obtained by transformation with a vector comprising a nucleotide sequence having a region homologous to any one of the genes (a) to (d), a nucleotide sequence having a region homologous to the promoter of any one of the genes (a) to (d), and/or a nucleotide sequence having a region homologous to a terminator of any one of the genes (a) to (d).

(3) The host cell according to the above (2), wherein the vector comprises a nucleotide sequence encoding a target protein.
(4) The host cell according to the above (2), further comprising a vector comprising a nucleotide sequence encoding a target protein.
(5) The host cell according to any one of the above (1) to (4), having a reduced ability to utilize methanol relative to a parent cell.
(6) The host cell according to any one of the above (1) to (5), which is obtained by transformation with a vector comprising any one of the following nucleotide sequences (e) to (h):
(e) a nucleotide sequence encoding an amino acid sequence as set forth in SEQ ID NO: 30,
(f) a nucleotide sequence encoding an amino acid sequence comprising a substitution, deletion, and/or addition of one or multiple amino acids with respect to the amino acid sequence shown in the above (e),
(g) a nucleotide sequence encoding an amino acid sequence having a sequence identity of 85% or more to the amino acid sequence shown in the above (e), and
(h) a nucleotide sequence of a nucleic acid hybridizing under a stringent condition to a nucleic acid consisting of a nucleotide sequence complementary to a nucleotide sequence encoding the amino acid sequence shown in the above (e).
(7) The host cell according to the above (6), which is a yeast, a bacterium, a fungus, an insect cell, an animal cell, or a plant cell.
(8) The host cell according to the above (7), wherein the yeast is a methanol-utilizing yeast, a fission yeast, or a budding yeast.
(9) The host cell according to the above (8), wherein the methanol-utilizing yeast is a yeast belonging to the genus *Komagataella* or a yeast belonging to the genus *Ogataea*.
(10) A method for producing a target protein, comprising culturing the cells according to any one of the above (3) to (9), and collecting a target protein from a culture mixture.
(11) The method according to the above (10), wherein the target protein is a heterologous protein.
(12) The method according to the above (10) or (11), wherein the culturing is performed in a culture mixture comprising one or more carbon sources selected from the group consisting of glucose, glycerol, and methanol.

The present description includes part or all of the contents as disclosed in Japanese Patent Application No. 2016-243198, which is a priority document of the present application.

According to one or more embodiments of the present invention, the ability to utilize methanol of a host cell can be reduced. Further, according to one or more embodiments of the present invention, a method for efficiently producing a target protein is provided.

DETAILED DESCRIPTION OF EMBODIMENTS

Hereinafter, one or more embodiments of the present invention will be described in detail.

One or more embodiments of the present invention relate to a host cell, wherein any one of the following genes (a) to (d) is inactivated:
(a) a gene comprising a nucleotide sequence as set forth in SEQ ID NO: 34,
(b) a gene comprising a nucleotide sequence of a nucleic acid hybridizing under a stringent condition to a nucleic acid consisting of a nucleotide sequence complementary to the nucleotide sequence as set forth in SEQ ID NO: 34,
(c) a gene comprising a nucleotide sequence having a sequence identity of 85% or more to the nucleotide sequence as set forth in SEQ ID NO: 34, and
(d) a gene encoding an amino acid sequence having a sequence identity of 85% or more to an amino acid sequence as set forth in SEQ ID NO: 33.

In one or more embodiments of the present invention, hybridization of two nucleic acids under a stringent condition has, for example, the following meanings. For example, when a nucleic acid X immobilized on a filter is hybridized to a nucleic acid Y having a sequence identity of 85% or more to the nucleic acid X in the presence of 0.7 to 1.0 M NaCl at 65° C., and thereafter, the resulting filter is washed using a 2×SSC solution (wherein a 1×SSC solution consists of 150 mM sodium chloride and 15 mM sodium citrate), if the nucleic acid Y can be obtained as a nucleic acid binding onto the filter, the nucleic acid Y can be referred to as a "nucleic acid hybridizing under a stringent condition to the nucleic acid X." It can also be said that the nucleic acid X and the nucleic acid Y "hybridize to each other under a under stringent condition." As the concentration of the SSC solution is decreased, it can be expected that nucleic acids having a higher sequence identity will hybridize to each other. Accordingly, in one or more embodiments, the nucleic acid Y can be obtained as a nucleic acid binding onto a filter by washing the filter, preferably with a 1×SSC solution at 65° C., more preferably with a 0.5×SSC solution at 65° C., even more preferably with a 0.2×SSC solution at 65° C., and further preferably with a 0.1×SSC solution at 65° C. Moreover, hybridization of nucleic acids having a higher sequence identity to each other can be expected, as the temperature is increased. Accordingly, in one or more embodiments, the nucleic acid Y can be obtained as a nucleic acid binding onto a filter by washing the filter, preferably with a 2×SSC solution at 70° C., more preferably with a 2×SSC solution at 75° C., even more preferably with a 2×SSC solution at 80° C., and further preferably with a 2×SSC solution at 85° C. The nucleic acid X serving as a reference may be a nucleic acid X derived from a colony or a plaque.

In one or more embodiments of the present invention, the sequence identity between nucleotide sequences or between amino acid sequences can be obtained according to methods well known to a person skilled in the art, or by using sequence analysis software. Examples of such a method include the blastn program or blastp program of BLAST algorithm, and the fasta program of FASTA algorithm. In one or more embodiments of the present invention, the "sequence identity" of a certain evaluation target nucleotide sequence to a nucleotide sequence X means a value obtained by aligning the nucleotide sequence X and the evaluation target nucleotide sequence (alignment), introducing a gap into the sequences, as necessary, so that the nucleotide identity of the two sequences becomes highest, and then indicating the frequency having the same nucleotides at the same site in the nucleotide sequences comprising the gap with %. In one or more embodiments of the present invention, the "sequence identity" of a certain evaluation target amino acid sequence to an amino acid sequence X means a value obtained by aligning the amino acid sequence X and the evaluation target amino acid sequence (alignment), introducing a gap into the sequences, as necessary, so that the amino acid identity of the two sequences becomes highest, and then indicating the frequency having the same amino acids at the same site in the amino acid sequences comprising the gap with %.

The sequence identity between the nucleotide sequence of the above-described gene and the nucleotide sequence as set forth in SEQ ID NO: 34 may be 85% or more, preferably 90% or more, more preferably 95% or more, further preferably 96% or more, particularly preferably 97% or more, and most preferably 98% or more, or 99% or more.

In one or more embodiments of the present invention, the "nucleic acid" may also be referred to as a "polynucleotide," and it may indicate DNA or RNA, and typically indicates DNA.

In the present description, the "gene" includes not only DNA in nucleic acids possessed by host cells, but it also includes the mRNA and cDNA thereof, and it is typically DNA, and is particularly genomic DNA. The functional regions of the "gene" are not particularly limited, and thus, for example, the gene may comprise only exons, or may also comprise both exons and introns.

The "nucleotide sequence as set forth in SEQ ID NO: 34" of the above (a), the "nucleotide sequence of a nucleic acid hybridizing under a stringent condition to a nucleic acid consisting of a nucleotide sequence complementary to the nucleotide sequence as set forth in SEQ ID NO: 34" of the above (b), and the "nucleotide sequence having a sequence identity of 85% or more to the nucleotide sequence as set forth in SEQ ID NO: 34" of the above (c) may each be a nucleotide sequence consisting of a plurality of exons connected with one another (e.g., a cDNA nucleotide sequence). In such a case, each of the gene (a), the gene (b) and the gene (c) may be DNA or RNA comprising a nucleotide sequence formed by further inserting and/or adding the nucleotide sequences of one or more introns into the above-described nucleotide sequence.

In the present description, DNA and RNA may be a double strand or a single strand. In the case of using a term such as a gene, DNA, RNA, a polynucleotide or a nucleic acid having a predetermined nucleotide sequence, these terms include a gene, DNA, RNA, a polynucleotide or a nucleic acid having a nucleotide sequence complementary to the predetermined nucleotide sequence, unless otherwise specified. Further, when such a gene, a polynucleotide or a nucleic acid is RNA, the nucleotide symbol "T" shown in the sequence listing shall be replaced with "U."

In one or more embodiments of the present invention, the "nucleotide sequence encoding an amino acid sequence" means a nucleotide sequence designed with respect to a polypeptide consisting of an amino acid sequence, based on the codon table. This nucleotide sequence brings on generation of the polypeptide as a result of transcription and translation.

In one or more embodiments of the present invention, the term "polypeptide" means two or more amino acids that bind to one another via peptide bonds. The polypeptide includes a protein, and also, those having a short chain length called a peptide or an oligopeptide.

In one or more embodiments of the present invention, the term "inactivation" includes a state in which the function of a gene is lost, or a state in which the function of a gene is reduced. In addition, it also includes a state in which the expression level of mRNA as a transcription product of the gene or a polypeptide as a translation product thereof is reduced, and a state in which the gene does not normally function as mRNA or a protein. The expression level of mRNA can be quantified according to any method, such as a real-time PCR method, an RNA-Seq method, Northern hybridization, and a hybridization method of utilizing a DNA array. The expression of a polypeptide can be quantified by using an antibody recognizing the polypeptide, a staining compound having binding ability to the polypeptide, etc. Other than the aforementioned quantification methods, conventional methods used by persons skilled in the art may also be applied.

As a means for inactivating a gene, a DNA mutation treatment using a drug or ultraviolet ray, site-specific mutagenesis using PCR, RNAi, protease, homologous recombination, or other techniques can be utilized. Inactivating a gene may include performing a modification (deletion, substitution, addition, or insertion) of a nucleotide sequence in the ORF of the gene, and/or performing a modification (deletion, substitution, addition, or insertion) of a nucleotide sequence in a region controlling initiation or termination of transcription, such as a promoter region, an enhancer region or a terminator region. Besides, the site on which the above-described deletion, substitution, addition or insertion is performed, or the nucleotide sequence to be deleted, substituted, added or inserted is not particularly limited, as long as the normal function of the gene can be suppressed. The gene to be inactivated may be a gene on the chromosome of a host cell, or may also be a gene outside of the chromosome of a host cell. In one or more embodiments, the gene to be inactivated is preferably the gene on the chromosome.

The "modification of a nucleotide sequence" according to one or more embodiments of the present invention can be carried out by applying a means such as insertion of a gene according to homologous recombination or site-specific mutagenesis. Examples of such means include substitution of a promoter located upstream of the gene with a promoter having lower activity, modification of a codon that is not suitable for a host cell, and introduction of a vector comprising a sequence upstream of a gene to be disrupted, a selective marker gene sequence, and a sequence downstream of a gene to be disrupted, ligated to one another. Herein, the "sequence upstream of a gene to be disrupted" means, for example, a nucleotide sequence located on the side upstream of the gene to be disrupted in the chromosomal genomic DNA of a host cell. On the other hand, the "sequence downstream of a gene to be disrupted" means, for example, a nucleotide sequence located on the side downstream of the gene to be disrupted in the chromosomal genomic DNA of a host cell.

The degree of a reduction in the expression level by the inactivation, according to one or more embodiments of the present invention, is not particularly limited, as long as the productivity of a target protein is improved. The expression level may be preferably reduced at a degree of 5% or more, 10% or more, 20% or more, 30% or more, 40% or more, 50% or more, 60% or more, 70% or more, 80% or more, 90% or more, or 95% or more. Besides, it is known to a person skilled in the art that, as mentioned above, a gene can be inactivated when the normal function of the gene product is lost, and the inactivation does not necessarily require the expression level of the gene to be reduced. Accordingly, the degree of a reduction in the expression level of a gene is only one criterion for determining inactivation.

In the present description, the "host cell" means a cell that is transformed by introduction of a vector therein, and it is referred to as a "host" or a "transformant." In the present description, the host cell before and after transformation is simply referred to as a "cell" at times. The cell used as a host is not particularly limited, as long as it is a cell into which a vector can be introduced.

The "gene comprising the nucleotide sequence as set forth in SEQ ID NO: 34" has been found as a result of the comprehensive analysis of the nucleotide sequences of four chromosomal DNAs of *Komagataella pastoris* (ATCC76273 strains: ACCESSION Nos. FR839628 to FR839631 (J. Biotechnol. 154 (4), 312-320 (2011), and GS115 strains: ACCESSION Nos. FN392319 to FN392322 (Nat. Biotechnol. 27 (6), 561-566 (2009)). Specifically, the present inventor has searched for a polypeptide causing a reduction in methanol utilization as a result of inactivation, and a polynucleotide comprising a nucleotide sequence encoding the amino acid sequence thereof. As a result, the present inventor has found, in ATCC76273 strains, a polypeptide having the amino acid sequence as set forth in SEQ ID NO: 33 (ACCESSION No. CCA41122), and a polynucleotide comprising the nucleotide sequence as set forth in SEQ ID NO: 34 encoding the aforementioned polypeptide. In the Examples as described later, the present inventors have introduced a vector for inactivating a gene consisting of the above-described nucleotide sequence into a host, and have then confirmed that the ability to utilize methanol of the host has been reduced and the productivity of a target protein has been improved by the introduction of the vector.

In the present description, an increase in the amount of a protein produced from a host cell may be, for example, 1.01 times, 1.02 times, 1.03 times, 1.04 times, 1.05 times, 1.1 times, 1.2 times, 1.3 times, 1.4 times, 1.5 times, 1.6 times, 1.7 times, 1.8 times, 1.9 times, 2 times, 2.5 times, 3 times, 3.5 times, 4 times, 4.5 times, or 5 times or more, or may be 100 times, 90 times, 80 times, 70 times, 60 times, 50 times, 40 times, 30 times, 20 times, 10 times, 9 times, 8 times, 7 times, 6 times, or 5 times or less, with respect to the amount of a protein produced from a parent cell or a wild-type strain. When a protein is produced according to secretory production, the amount of a total protein secreted from cells can be easily determined by analyzing a culture supernatant of cells according to a method known to a person skilled in the art, such as a Bladford method, a Lowry method, and a BCA method. The amount of a specific protein secreted from cells can be easily determined by analyzing a culture supernatant of cells according to an ELISA method or the like.

In the present description, the "parent cell" or the "wild-type strain" means a host cell or strain, on which a treatment of changing the expression of a gene comprising the nucleotide sequence described in any one of the above (a) to (d) is not performed. Accordingly, the "parent cell" or the "wild-type strain" described in the present description includes a host cell or strain, in which a nucleotide sequence other than the nucleotide sequence described in any one of the above (a) to (d) is modified.

As an example of inactivating the gene consisting of the nucleotide sequence as set forth in SEQ ID NO: 34, there is a method which comprises: preparing a PCR product using primer 19 and primer 20 respectively comprising, as an internal sequence, a nucleotide sequence having a sequence identity of 100% to 97 bp of a promoter located upstream of the gene consisting of the nucleotide sequence as set forth in SEQ ID NO: 34 (e.g., nucleotides at positions 1 to 97 shown in SEQ ID NO: 31) and a nucleotide sequence having a sequence identity of 100% to 98 bp of a complementary sequence of a terminator located downstream of the gene consisting of the nucleotide sequence as set forth in SEQ ID NO: 34 (e.g., nucleotides at positions 1 to 98 shown in SEQ ID NO: 32); and then using the PCR product as a vector to transform a yeast belonging to the genus *Komagataella*, as described in the Examples later.

The "gene encoding an amino acid sequence having a sequence identity of 85% or more to an amino acid sequence as set forth in SEQ ID NO: 33" means a gene consisting of a nucleotide sequence that is designed based on a polypeptide consisting of an amino acid sequence having a sequence identity of 85% or more to the amino acid sequence as set forth in SEQ ID NO: 33, with reference to the codon table, and it is, for example, a gene shown in SEQ ID NO: 34. Inactivating this gene leads to a reduction in the ability to utilize methanol and an improvement of the productivity of a target protein. The above-described sequence identity may be 85% or more, preferably 90% or more, more preferably 95% or more, further preferably 96% or more, particularly preferably 97% or more, and most preferably 98% or more, or 99% or more.

The host cell according to one or more embodiments of the present invention is preferably obtained by transformation with a vector comprising at least any one of a nucleotide sequence having a region homologous to any one of the genes (a) to (d), a nucleotide sequence having a region homologous to a promoter of any one of the genes (a) to (d), and/or a nucleotide sequence having a region homologous to a terminator of any one of the genes (a) to (d).

In one or more embodiments of the present invention, any one of the genes (a) to (d) on the chromosome of a host cell can be inactivated by transforming a parent cell with a vector comprising at least any one of a nucleotide sequence having a region homologous to any one of the genes (a) to (d), a nucleotide sequence having a region homologous to a promoter of any one of the genes (a) to (d), and a nucleotide sequence having a region homologous to a terminator of any one of the genes (a) to (d). In addition, as such a vector, a vector into which all of the nucleotide sequences having different homologous regions are incorporated may be used, or vectors into each of which one nucleotide sequence having one homologous region is incorporated may also be used.

In one or more embodiments of the present invention, the above-described "vector into which all of the nucleotide sequences having different homologous regions are incorporated" may be a single vector comprising all of a nucleotide sequence having a region homologous to any one of the genes (a) to (d), a nucleotide sequence having a region homologous to a promoter of any one of the genes (a) to (d), and a nucleotide sequence having a region homologous to a terminator of any one of the genes (a) to (d).

In one or more embodiments of the present invention, the above-described "vectors into each of which one nucleotide sequence having one homologous region is incorporated" may be a combination of a first vector comprising a nucleotide sequence having a region homologous to any one of the genes (a) to (d), a second vector comprising a nucleotide sequence having a region homologous to a promoter of any one of the genes (a) to (d), and a third vector comprising a nucleotide sequence having a region homologous to a terminator of any one of the genes (a) to (d). In this case, upon the transformation of a host cell, the first to third vectors may be simultaneously introduced into the host cell, or these vectors may also be introduced therein, successively.

The vector according to one or more embodiments of the present invention can be a cyclic vector, a linear vector, a plasmid, an artificial chromosome, etc.

In one or more embodiments of the present invention, the vector is an artificially constructed nucleic acid molecule. The nucleic acid molecule constituting the vector according to one or more embodiments of the present invention may be generally DNA, and preferably double-stranded DNA. It may be cyclic or linear DNA. In general, the vector according to one or more embodiments of the present invention may comprise a cloning site comprising one or more restriction enzyme recognition sites, an overlapping region for utilizing a cloning system such as the In-Fusion Cloning System manufactured by Clontech and the Gibson Assembly System manufactured by New England Biolabs, a nucleotide sequence of an endogenous gene, a nucleotide sequence encoding a polypeptide consisting of the amino acid sequence of a target protein, and the nucleotide sequence of a selective marker gene (for example, an auxotrophic complementary gene, or a drug resistance gene), in addition to a predetermined nucleotide sequence (i.e., the aforementioned nucleotide sequence shown in any one of the above (a) to (d), the aforementioned nucleotide sequence having a region homologous to a promoter of any one of the genes (a) to (d), the aforementioned nucleotide sequence having a region homologous to a terminator of any one of the genes (a) to (d), or a nucleotide sequence containing a plurality of these nucleotide sequences ligated to one another (the nucleotide sequences may be ligated to one another via a further nucleotide sequence having a suitable length)). Examples of the linear vector include: PCR products having the nucleotide sequences of auxotrophic complementary genes such as a URA3 gene, a LEU2 gene, an ADE1 gene, a HIS4 gene, or an ARG4 gene, drug resistance genes such as a G418 resistance gene, a Zeocin (registered trademark) resistance gene, a hygromycin resistance gene, a Clone NAT resistance gene, or a blasticidin S resistance gene; and cyclic vectors or plasmids, which are cleaved with suitable restriction enzymes and are then linearized. Examples of the plasmid that can be used herein include a YEp vector, a YRp vector, a YCp vector, pPICHOLI (http://www.mobitec.com/cms/products/bio/04_vector_sys/p_picholi_shuttle_vector.html), pHIP (Journal of General Microbiology (1992), 138, 2405-2416. Chromosomal targeting of replicating plasmids in the yeast *Hansenula polymorpha*), pHRP (see the above-described publication regarding pHIP), pHARS (Molecular and General Genetics MGG February 1986, Volume 202, Issue 2, pp 302-308, Transformation of the methylotrophic yeast *Hansenula polymorpha* by autonomous replication and integration vectors), *Escherichia coli*-derived plasmid vector (pUC18, pUC19, pBR322, or pBluescript, pQE), and *Bacillus subtilis*-derived plasmid vector (pHY300PLK or pMTLBS72). In general, the artificial chromosome indicates an artificial chromosomal vector comprising a centromere DNA sequence, a telomere DNA sequence, or autonomously replicating sequence (ARS). In the case of a yeast, the artificial chromosome may be, for example, a yeast artificial chromosome (YAC vector), and such yeast artificial chromosome has been developed from *Saccharomyces cerevisiae, Schizosaccharomyces pombe* and the like. By using the centromere DNA sequence described in International Publication No. WO 2016/088824, an artificial chromosome derived from *Komagataella pastoris* can be constructed.

A typical example of the vector according to one or more embodiments of the present invention may be a linear vector comprising a first homologous region homologous to a first nucleotide sequence on an upstream side and a second homologous region homologous to a second nucleotide sequence on a downstream side, wherein the first nucleotide sequence is a nucleotide sequence of a portion of regions comprising any one of the genes (a) to (d), a promoter of any one of the genes (a) to (d), and a terminator of any one of the genes (a) to (d) in the genomic DNA of a host cell, and wherein the second nucleotide sequence is a nucleotide sequence of another portion of the regions located downstream of the first nucleotide sequence. In this linear vector, one or more nucleotide sequences, such as the nucleotide sequence of an endogenous gene, a nucleotide sequence encoding a polypeptide consisting of an amino acid sequence of a target protein, and a nucleotide sequence of a selective marker gene, as described above, may be preferably present between the first homologous region and the second homologous region. The first nucleotide sequence may be preferably the nucleotide sequence of at least a portion of a promoter of any one of the genes (a) to (d) in the genomic DNA of a host cell. For example, when the host cell is *Komagataella pastoris*, the first nucleotide sequence can be a nucleotide sequence consisting of nucleotides at positions 1 to 97 shown in SEQ ID NO: 31. On the other hand, the second nucleotide sequence may be preferably a nucleotide sequence of at least a portion of a terminator of any one of the genes (a) to (d) in the genomic DNA of a host cell. For example, when the host cell is *Komagataella pastoris*, the second nucleotide sequence can be a nucleotide sequence consisting of nucleotides at positions 1 to 98 shown in SEQ ID NO: 32.

In one or more embodiments of the present invention, the "transformation" means introduction of the above-described vector into a cell. As a method of introducing a vector into a host cell, namely, as a transformation method, a known method can be applied, as appropriate. For example, when a yeast cell is used as a host, an electroporation method, a lithium acetate method, a spheroplast method, etc. may be applied, but the method is not particularly limited thereto. For example, as a transformation method for *Komagataella pastoris*, the electroporation method described in "High efficiency transformation by electroporation of *Pichia pastoris* pretreated with lithiumacetate and dithiothreitol" (Biotechniques. 2004 January; 36(1): 152-4.) may be applied.

In one or more embodiments of the present invention, in a case where a yeast belonging to the genus *Komagataella* is transformed with a vector, a selective marker gene such as an auxotrophic complementary gene or a drug resistance gene may be preferably used. The selective marker is not particularly limited. In transformation of a yeast belonging to the genus *Komagataella*, if an auxotrophic complementary gene such as a URA3 gene, a LEU2 gene, an ADE1 gene, a HIS4 gene, or an ARG4 gene is used, a transformant can be selected from an auxotrophic strain for uracil, leucine, adenine, histidine or arginine, as a result of the recovery of the phenotype of the prototrophic strain. On the other hand, by using a drug resistance gene such as a G418 resistance gene, a Zeocin (registered trademark) resistance gene, a hygromycin resistance gene, a Clone NAT resistance gene, or a blasticidin S resistance gene, a transformant can be selected depending on resistance on a medium each comprising G418, Zeocin (registered trademark), hygromycin, Clone NAT, or blasticidin S. Besides, the auxotrophic selective marker used in the production of a yeast host cannot be used, when the selective marker is not disrupted in the host. In this case, it is appropriate that the selective marker is disrupted in the host. As a method of disrupting the selective marker, a method known to a person skilled in the art can be used.

In one or more embodiments of the present invention, when a vector is incorporated into a chromosome, the vector may be preferably produced in the form of DNA comprising a plurality of regions homologous to regions in the chromosome, as described in the Examples below. As a method of incorporating a vector into the chromosome, non-specific incorporation that does not utilize a homologous region, or incorporation that utilizes one homologous region, or a double crossover-type incorporation that utilizes two homologous regions may be applied.

In one or more embodiments of the present invention, in the case of incorporation utilizing homologous regions, for example, as described in the present Examples, transformation can be carried out by using a vector comprising a selective marker gene sequence and homologous regions disposed on both sides of the selective marker gene sequence respectively. For example, for the purpose of disrupting a gene, a vector comprising a selective marker gene, a nucleotide sequence comprising a region homologous to a promoter of the gene to be disrupted ligated to the upstream of the selective marker gene, and a nucleotide sequence comprising a region homologous to a terminator of the gene to be disrupted ligated to the downstream of the selective marker gene, can be incorporated into the chromosome.

In one or more embodiments of the present invention, the copy number of a vector per chromosome is not particularly limited. In addition, the position on the chromosome into which the vector is incorporated is not particularly limited, as long as the gene according to one or more embodiments of the present invention is inactivated. With regard to the position of a transformant into which two or more copies of vectors are incorporated, a plurality of vectors may be incorporated into the same position, or individual copies may be each incorporated into different positions.

The "nucleotide sequence having a homologous region" according to one or more embodiments of the present invention may be a nucleotide sequence having at least a portion of a nucleotide sequence of interest, which has a sequence identity of 50% or more to the nucleotide sequence of interest. In one or more embodiments, it may be a nucleotide sequence having a sequence identity of more preferably 70% or more, even more preferably 80% or more, particularly preferably 85% or more, more particularly preferably 90% or more, further particularly preferably 95% or more, and most preferably 100% to the nucleotide sequence of interest. Moreover, the length of the nucleotide sequence having a homologous region is not particularly limited, as long as it is a nucleotide sequence with a length of 20 bp or more having a region homologous to the nucleotide sequence of interest, which can be used for homologous recombination. In some embodiments, the length of the nucleotide sequence having a homologous region may be preferably 0.1% or more of the length of the nucleotide sequence of interest, and it may be more preferably 0.5% or more, 1% or more, 1.5% or more, 2% or more, 2.5% or more, 3% or more, 3.5% or more, 4% or more, 4.5% or more, 5% or more, 5.5% or more, 6% or more, 6.5% or more, 7% or more, 7.5% or more, 8% or more, 8.5% or more, 9% or more, 9.5% or more, 10% or more, 15% or more, 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 95% or more, or 100% of the length of the nucleotide sequence of interest.

The "promoter of any one of the genes (a) to (d)" according to one or more embodiments of the present invention is a nucleotide sequence, which is present upstream of any one of the genes (a) to (d) on the chromosome and regulates the expression level of the gene product. In some specific embodiments, the promoter of any one of the genes (a) to (d) means at least a portion of the nucleotide sequence that is up to 5000 bp upstream of the start codon of any one of the genes (a) to (d).

The "terminator of any one of the genes (a) to (d)" according to one or more embodiments of the present invention is a nucleotide sequence, which is present downstream of any one of the genes (a) to (d) on the chromosome and regulates the expression level of the gene product. In some specific embodiments, the terminator of any one of the genes (a) to (d) means at least a portion of the nucleotide sequence that is up to 5000 bp downstream of the stop codon of any one of the genes (a) to (d).

The host cell according to one or more embodiments of the present invention may be preferably obtained by transforming a parent cell with a vector comprising at least any one of a nucleotide sequence having a region homologous to any one of the genes (a) to (d), a nucleotide sequence having a region homologous to a promoter of any one of the genes (a) to (d), and/or a nucleotide sequence having a region homologous to a terminator of any one of the genes (a) to (d), and further comprising a nucleotide sequence encoding a polypeptide consisting of an amino acid sequence of a target protein upstream or downstream of the aforementioned nucleotide sequence.

Transforming a parent cell with a vector in which a nucleotide sequence encoding a polypeptide consisting of an amino acid sequence of a target protein is disposed upstream or downstream of a nucleotide sequence having a region homologous to any one of the genes (a) to (d), a nucleotide sequence having a region homologous to a promoter of any one of the genes (a) to (d), and/or a nucleotide sequence having a region homologous to a terminator of any one of the genes (a) to (d), can produce a host cell with improved productivity of the target protein. Furthermore, by using a vector comprising the nucleotide sequences having individual homologous regions and a nucleotide sequence encoding a polypeptide consisting of an amino acid sequence of a target protein disposed upstream and/or downstream of the aforementioned nucleotide sequences, the operability of transformation can be improved.

In one or more embodiments of the present invention, the "target protein" may be a protein produced from a cell into which the vector according to one or more embodiments of the present invention is introduced. The target protein may be either a protein endogenous to the host, or a protein heterologous to the host. Examples of the target protein include enzymes derived from microorganisms, and proteins generated by animals or plants that are multicellular organisms. Specific examples of the target protein include phytase, Protein A, Protein G, Protein L, amylase, glucosidase, cellulase, lipase, protease, glutaminase, peptidase, nuclease, oxidase, lactase, xylanase, trypsin, pectinase, isomerase, fibroin, and a fluorescent protein, but are not limited thereto. In particular, proteins for use in the treatment of humans and/or animals may be preferable. Specific examples of such proteins for use in the treatment of humans and/or animals include a hepatitis B virus surface antigen, hirudin, an antibody, a human antibody, a partial antibody, a humanized antibody, serum albumin, human serum albumin, an epidermal growth factor, a human epidermal growth factor, insulin, growth hormone, erythropoietin, interferon, a blood coagulation factor VIII, a granulocyte colony stimulating factor (G-CSF), a granulocyte-macrophage colony stimulating factor (GM-CSF), thrombopoietin, IL-1, IL-6, a tissue plasminogen activator (TPA), urokinase, leptin, and a stem cell growth factor (SCF).

Herein, the "antibody" may be a heterotetramer protein constituted with L chains and H chains, each of which is formed of two polypeptide chains, which are bind to each other via a disulfide bond. The antibody is not particularly limited, as long as it has an ability to bind to a specific antigen.

Herein, the "partial antibody" may be a Fab antibody, a (Fab) 2 antibody, an scFv antibody, a diabody, a derivative thereof, or the like. The partial antibody is not particularly limited, as long as it has an ability to bind to a specific antigen. The Fab antibody means a heteromeric protein, in which the L chain of an antibody binds to a Fd chain via an S—S bond, or a heteromeric protein, in which the L chain of an antibody is associated with a Fd chain without an S—S-bond. The Fab antibody is not particularly limited, as long as it has an ability to bind to a specific antigen.

Amino acids constituting the above-described target protein may be natural amino acids, or may be non-natural amino acids, or may also be modified. In addition, the amino acid sequence of the protein may be subjected to artificial modification, or may also be designed de novo.

The host cell according to one or more embodiments of the present invention may preferably be obtained by transforming a parent cell with a vector comprising at least any one of a nucleotide sequence having a region homologous to any one of the genes (a) to (d), a nucleotide sequence having a region homologous to a promoter of any one of the genes (a) to (d), and/or a nucleotide sequence having a region homologous to a terminator of any one of the genes (a) to (d), and a vector comprising a nucleotide sequence encoding a polypeptide consisting of the amino acid sequence of a target protein.

Transforming a cell with a vector comprising at least any one of a nucleotide sequence having a region homologous to any one of the genes (a) to (d), a nucleotide sequence having a region homologous to a promoter of any one of the genes (a) to (d), and/or a nucleotide sequence having a region homologous to a terminator of any one of the genes (a) to (d), and a vector comprising a nucleotide sequence encoding a polypeptide consisting of an amino acid sequence of a target protein, can produce a host cell with improved productivity of the target protein. Further, by using both the vector for inactivation and the vector comprising a nucleotide sequence encoding a polypeptide consisting of the amino acid sequence of a target protein, separately, the following can be achieved: one or more copies of the vectors comprising a nucleotide sequence encoding a target protein are introduced into positions other than the positions of any one of the genes (a) to (d), so that the expression level is increased; a plasmid or an artificial chromosome comprising one or more copies of the nucleotide sequences encoding a polypeptide consisting of the amino acid sequence of a target protein is introduced, so that the expression level is increased; or upon disruption of an auxotrophic complementary gene or a drug resistance gene that has been used in inactivation of any one of the genes (a) to (d) for breed improvement, disruption of the nucleotide sequence encoding a polypeptide consisting of the amino acid sequence of a target protein is prevented. Therefore, the productivity of a target protein can be efficiently improved.

The host cell according to one or more embodiments of the present invention is characterized in that its ability to utilize methanol is reduced in comparison to that of the parent cell.

In one or more embodiments of the present invention, the "methanol utilization" means that a host cell digests methanol as a carbon source. Whether or not such methanol utilization is reduced can be confirmed, for example, by culturing cells in a medium containing methanol as a carbon source and then measuring the number of cells, or for example, by measuring the amount of methanol remaining in the culture mixture or the amount of oxygen dissolved in the culture mixture, and then comparing the measured amount with that of a non-modified strain such as a parent cell or a wild-type strain.

One or more embodiments of the present invention relate to a host cell obtained by being further transformed with a vector comprising any one of the following nucleotide sequences (e) to (h):

(e) a nucleotide sequence encoding an amino acid sequence as set forth in SEQ ID NO: 30, (f) a nucleotide sequence encoding an amino acid sequence comprising a substitution, deletion, and/or addition of one or multiple amino acids with respect to the amino acid sequence shown in the above (e), (g) a nucleotide sequence encoding an amino acid sequence having a sequence identity of 85% or more to the amino acid sequence shown in the above (e), and (h) a nucleotide sequence of a nucleic acid hybridizing under a stringent condition to a nucleotide sequence complementary to a nucleotide sequence encoding the amino acid sequence shown in the above (e).

The "amino acid sequence as set forth in SEQ ID NO: 30" is the amino acid sequence of a polypeptide PpMPP1 that is a transcriptional factor for activating a methanol-inducible promoter, which has been found by the present inventor (ACCESSION No. CCA39317, International Publication No. WO 2012/102171). The "nucleotide sequence encoding the amino acid sequence as set forth in SEQ ID NO: 30" is, for example, the nucleotide sequence as set forth in SEQ ID NO: 5. However, this nucleotide sequence is not particularly limited, as long as it encodes the amino acid sequence as set forth in SEQ ID NO: 30. In the Examples as described later, the present inventors have confirmed that the productivity of a target protein is further improved by further transforming the host cell, in which any one of the genes (a) to (d) has been inactivated, with a vector comprising any one of the above nucleotide sequences (e) to (h), and thus allowing the polypeptide PpMPP1 having the amino acid sequence as set forth in SEQ ID NO: 30 to express at a high level.

In one or more embodiments of the present invention, the term "one or multiple" used regarding a substitution, deletion, insertion and/or addition of amino acids means, for example, in the amino acid described in (f), 1 to 280, 1 to 250, 1 to 200, 1 to 190, 1 to 160, 1 to 130, 1 to 100, 1 to 75, 1 to 50, 1 to 25, 1 to 20, 1 to 15, 1 to 10, 1 to 7, 1 to 5, 1 to 4, 1 to 3, or 1 or 2 amino acids. The amino acid sequence described in (f) is, for example, a partial amino acid sequence consisting of 1 to 5, 1 to 10, 1 to 25, 1 to 50, 1 to 75, 1 to 100, 1 to 125, 1 to 150, 1 to 175, 1 to 200, 1 to 225, 1 to 250, 1 to 275, or 1 to 300 contiguous amino acids in the amino acid sequence as set forth in SEQ ID NO: 30.

The "sequence identity of 85% or more" described in (g) may be a sequence identity of more preferably 90% or more, even more preferably 95% or more, further preferably 96% or more, still further preferably 97% or more, still further preferably 98% or more, and most preferably 99% or more.

In one or more embodiments of the present invention, the "expression" means transcription and translation of a nucleotide sequence that brings on generation of a polypeptide. The expression may be in almost a constant state without depending on external stimulation, growth conditions, etc., or may also depend thereon. The promoter that drives the expression is not particularly limited, as long as it is a promoter driving the expression of a nucleotide sequence encoding a polypeptide.

In one or more embodiments of the present invention, the "expression at a high level" means that the amount of a polypeptide in a host cell or the amount of mRNA in a host cell is increased in comparison to the ordinary amount. The polypeptide or mRNA expressed at a high level can be confirmed, for example, by measuring the amount of a polypeptide utilizing an antibody recognizing the polypeptide, or by measuring the amount of mRNA according to an RT-PCR method, Northern hybridization, hybridization using a DNA array, or other method, and then comparing the measured amount with that of a non-modified strain such as a parent cell or a wild type strain.

The organism species of the host cell is not particularly limited, and examples thereof include yeasts, bacteria, fungi, insect cells, animal cells, and plant cells. Among these, yeasts may be preferable; a methanol-utilizing yeast, a fission yeast, and a budding yeast may be more preferable; and a methanol-utilizing yeast may be further preferable. In general, the methanol-utilizing yeast is defined as a yeast capable of being cultured by utilizing methanol as only carbon source. A yeast which has originally been a methanol-utilizing yeast but then has lost its methanol-utilizing ability is also included in the methanol-utilizing yeast according to one or more embodiments of the present invention.

Examples of the methanol-utilizing yeast include yeasts belonging to the genus *Pichia*, the genus *Ogataea*, the genus *Candida*, the genus *Torulopsis*, and the genus *Komagataella*. In one or more embodiments, a preferred example of the genus *Pichia* is *Pichia methanolica*. Examples of the genus *Ogataea* include *Ogataea angusta*, *Ogataea polymorpha*, *Ogataea parapolymorpha*, and *Ogataea minuta*. In one or more embodiments, a preferred example of the genus *Candida* is *Candida boidinii*. Examples of the genus *Komagataella* include *Komagataella pastoris* and *Komagataella phaffii*.

Among the above-described methanol-utilizing yeasts, yeasts belonging to the genus *Komagataella* or yeasts belonging to the genus *Ogataea* may be particularly preferable.

The yeasts belonging to the genus *Komagataella* may be preferably *Komagataella pastoris* and *Komagataella phaffii*. Both *Komagataella pastoris* and *Komagataella phaffii* are also referred to as an alias "*Pichia pastoris*."

Examples of the yeast strain that can be actually used as a host include yeast strains such as *Komagataella pastoris* ATCC76273 (Y-11430, CBS7435) and *Komagataella pastoris* X-33. These strains are available from American Type Culture Collection, Thermo Fisher Scientific, etc.

Examples of the genus *Ogataea* include *Ogataea angusta*, *Ogataea polymorpha*, and *Ogataea parapolymorpha*. These three strains are closely related species, and all of them are also referred to as an alias "*Hansenula polymorpha*," or an alias "*Pichia angusta*."

Examples of the actually usable yeast strain include yeast strains such as *Ogataea angusta* NCYC495 (ATCC14754), *Ogataea polymorpha* 8V (ATCC34438), and *Ogataea parapolymorpha* DL-1 (ATCC26012). These strains are available from American Type Culture Collection, etc.

Moreover, in one or more embodiments of the present invention, strains derived from these yeasts belonging to the genus *Komagataella* or the genus *Ogataea* can also be used. For example, in the case of a histidine auxotrophic strain, a *Komagataella pastoris* GS115 strain (available from Thermo Fisher Scientific) can be used, and in the case of leucine auxotrophic strains, BY4329 derived from NCYC495, BY5242 derived from 8V, BY5243 derived from DL-1 (all of these can be furnished from National BioResource Project), can be used for example. In one or more embodiments of the present invention, strains derived from these yeast strains can also be used.

One or more embodiments of the present invention relate to a method for producing a target protein, comprising culturing the above-described cells and collecting a target protein from a culture mixture.

Herein, the "culture mixture" means a cultured cell, a cultured cell mass, or a homogenate of a cell or a cell mass, as well as a culture supernatant. Accordingly, a method for producing a target protein by using the transformed yeast according to one or more embodiments of the present invention may be a method of culturing the above-described cells and accumulating a target protein in the cells, or a method of culturing the above-described cells and secreting and accumulating a target protein into a culture supernatant. In one or more embodiments, a method of secreting and accumulating a target protein into a culture supernatant is applied.

Conditions for culturing cells are not particularly limited, and the culture conditions may be selected, as appropriate, depending on the cells. In the culture, any medium can be used, as long as it is a medium supplemented with a nutrient source that can be utilized by the cells. Such a nutrient source may include: carbon sources including sugars such as glucose, sucrose or maltose, organic acids such as lactic acid, acetic acid, citric acid or propionic acid, alcohols such as methanol, ethanol or glycerol, hydrocarbons such as paraffin, oils such as soybean oil or rapeseed oil, or mixtures thereof; nitrogen sources such as ammonium sulfate, ammonium phosphate, urea, yeast extract, meat extract, peptone, or corn steep liquor; and further, other nutrient sources such as inorganic salts or vitamins. An ordinary culture medium that is appropriately prepared by mixing and blending these nutrient sources can be used. Furthermore, the culture may be either a batch culture or a continuous culture.

In one or more embodiments of the present invention, when the yeast belonging to the genus *Komagataella* or the yeast belonging to the genus *Ogataea* is used, the above-described carbon source may be one, or two or more selected from glucose, glycerol and methanol. In addition, these carbon sources may be present from the early stage of culture, or may be added during the culture.

In one or more embodiments, the transformant obtained by introducing the vector into the cells is cultured, so that a target protein can be accumulated in the host cell or the culture supernatant and can be then collected. As a method of collecting the target protein, known purification methods can be appropriately combined and used. For example, first, the transformed yeast is cultured in a suitable medium, and then, a cell mass is removed from the culture supernatant by centrifuging the culture mixture or performing a filtration treatment on the culture mixture. Thereafter, means such as salting out (ammonium sulfate precipitation, sodium phosphate precipitation, etc.), solvent precipitation (a protein fractional precipitation method using acetone, ethanol, or the like), dialysis, gel filtration chromatography, ion exchange chromatography, hydrophobic chromatography, affinity chromatography, reverse phase chromatography, and ultrafiltration are applied, alone or in combination, to the obtained culture supernatant, so that the target protein is collected from the culture supernatant.

Cell culture can be carried out under ordinary conditions. For example, in the case of yeast, the cells can be aerobically cultured at pH 2.5 to 10.0, in a temperature range from $10°$ C. to $48°$ C., for 10 hours to 10 days.

The collected target protein may be directly used. Alternatively, after the collection of the target protein, a modification for changing a pharmacological behavior, such as PEGylation, or a modification for adding a function of an enzyme or an isotope, may be performed on the target protein, and the modified target protein may be then used. In addition, various types of formulation treatments may also be used.

For the purpose of producing a non-secretory target protein by secretion out of the cells, a nucleotide sequence encoding a signal sequence may be introduced into the 5'-terminus of the target protein gene. The nucleotide sequence encoding a signal sequence is not particularly limited, as long as it encodes a signal sequence that can be expressed and secreted by yeast. Examples of the nucleotide sequence encoding a signal sequence include nucleotide sequences encoding Mating Factor α (MFα) of *Saccharomyces cerevisiae*, acid phosphatase (PHO1) of *Ogataea angusta*, acid phosphatase (PHO1) of *Komagataella pastoris*, invertase (SUC2) of *Saccharomyces cerevisiae*, PLB1 of *Saccharomyces cerevisiae*, or a signal sequence of bovine serum albumin (BSA), human serum albumin (HSA), or immunoglobulin.

In the present description, the "target protein," the productivity of which is to be improved, may be an endogenous protein endogenous to the host, or a heterologous protein heterologous to the host. In the present description, the "endogenous protein" means a protein produced by a host cell with no genetic modification during the culture thereof. In contrast, in the present description, the "heterologous protein" means a protein that is not generally expressed by a host cell with no genetic modification, or even if it is expressed, the expression level is not sufficient.

A promoter that enables expression of a target protein in the selected carbon source may be appropriately used, and thus, the promoter is not particularly limited.

Examples of the promoter for expressing a polypeptide in the presence of methanol as a carbon source include an AOX1 promoter, an AOX2 promoter, a CAT promoter, a DHAS promoter, an FDH promoter, an FMD promoter, a GAP promoter, and a MOX promoter, but are not particularly limited thereto.

Examples of the promoter for expressing a polypeptide in the presence of glucose or glycerol as a carbon source include a GAP promoter, a TEF promoter, a LEU2 promoter, a URA3 promoter, an ADE promoter, an ADH1 promoter, and a PGK1 promoter, but are not particularly limited thereto.

Herein, the "promoter" means a nucleotide sequence region located upstream of the predetermined nucleotide sequence as described above. Not only RNA polymerase, but also various transcription regulatory factors relating to promotion or suppression of the transcription bind to or act on this region, so that they read the predetermined nucleotide sequence as described above, and synthesize (transcribe) complementary RNA.

Hereinafter, one or more embodiments of the present invention will be described in detail in the following production examples, comparative examples, and examples. However, these examples are not intended to limit the scope of the present invention.

Production Example 1: Preparation of Various Genes Used in Preparation of Vectors General DNA recombination procedures used in the following examples are detailed in the following publication: Molecular Cloning 2nd Edition (Cold Spring Harbor Laboratory Press, 1989), Current Protocols in Molecular Biology (Greene Publishing Associates and Wiley-Interscience).

Moreover, in the following examples, plasmids used in the transformation of yeasts were prepared by introducing the constructed vector into *Escherichia coli* DH5α competent cells (manufactured by Takara Bio Inc.) and then culturing the obtained transformants to amplify them. Preparation of plasmids from plasmid-retaining strains was carried out using FastGene Plasmid Mini Kit (manufactured by NIPPON Genetics Co., Ltd.).

The AOX1 promoter (SEQ ID NO: 1), the AOX1 terminator (SEQ ID NO: 2), the HIS4 sequence (SEQ ID NO: 3), the GAP promoter (SEQ ID NO: 4), the nucleotide sequence encoding the polypeptide PpMPP1 (SEQ ID NO: 5), and the CCA38473 terminator (SEQ ID NO: 6), which were utilized in the construction of vectors, were prepared by PCR, using, as a template, a mixture of chromosomal DNAs of the *Komagataella pastoris* ATCC76273 strain (the nucleotide sequences of which are described in EMBL (The European Molecular Biology Laboratory) ACCESSION Nos. FR839628 to FR839631). The AOX1 promoter was prepared by PCR using primer 1 (SEQ ID NO: 7) and primer 2 (SEQ ID NO: 8); the AOX1 terminator was prepared by PCR using primer 3 (SEQ ID NO: 9) and primer 4 (SEQ ID NO: 10); the HIS4 sequence was prepared by PCR using primer 5 (SEQ ID NO: 11) and primer 6 (SEQ ID NO: 12); the GAP promoter was prepared by PCR using primer 7 (SEQ ID NO: 13) and primer 8 (SEQ ID NO: 14); the nucleotide sequence encoding the polypeptide PpMPP1 was prepared by PCR using primer 9 (SEQ ID NO: 15) and primer 10 (SEQ ID NO: 16); and the CCA38473 terminator was prepared by PCR using primer 11 (SEQ ID NO: 17) and primer 12 (SEQ ID NO: 18).

A promoter-regulated Zeocin (registered trademark) resistance gene (SEQ ID NO: 19), which was utilized in the construction of vectors, was prepared by PCR using synthetic DNA as a template. A promoter-regulated G418 resistance gene (SEQ ID NO: 20), which was utilized in the construction of vectors, was prepared by PCR using synthetic DNA as a template. An anti-β-galactosidase single-chain antibody gene (SEQ ID NO: 21) having a Mating Factor α prepro-signal sequence, which was utilized in the construction of vectors, was prepared by PCR using synthetic DNA as a template, based on the published sequence information (J Mol Biol. 1998 Jul. 3; 280(1): 117-27.).

PCRs were conducted with Prime STAR HS DNA Polymerase (manufactured by Takara Bio Inc.) under reaction conditions in accordance with its manual. Chromosomal DNA was prepared from a *Komagataella pastoris* ATCC76273 strain, using Kaneka Simple DNA Extraction Kit Version 2 (manufactured by Kaneka Corporation) under conditions in accordance with its manual.

Production Example 2: Construction of Anti-β-Galactosidase Single-Chain Antibody Expressing Vector A gene fragment (SEQ ID NO: 22) having the multi-cloning site of HindIII-BamHI-BglII-XbaI-EcoRI was totally synthesized, and the synthesized gene fragment was then inserted between the HindIII-EcoRI sites of pUC19 (manufactured by Takara Bio Inc., Code No. 3219), so as to construct pUC-1.

Moreover, a nucleic acid fragment comprising the AOX1 promoter (SEQ ID NO: 1) and BamHI-recognizing sequences added to both sides of the promoter was prepared by PCR using primers 1 (SEQ ID NO: 7) and 2 (SEQ ID NO: 8). The nucleic acid fragment was treated with BamHI, and it was then inserted into the BamHI site of pUC-1 to construct pUC-Paox.

Subsequently, a nucleic acid fragment comprising the AOX1 terminator (SEQ ID NO: 2) and XbaI-recognizing sequences added to both sides of the terminator was prepared by PCR using primers 3 (SEQ ID NO: 9) and 4 (SEQ ID NO: 10). The nucleic acid fragment was treated with XbaI, and it was then inserted into the XbaI site of pUC-Paox to construct pUC-PaoxTaox.

Subsequently, a nucleic acid fragment comprising the HIS4 sequence (SEQ ID NO: 3) and EcoRI-recognizing sequences added to both sides of the HIS4 sequence was prepared by PCR using primers 5 (SEQ ID NO: 11) and 6 (SEQ ID NO: 12). The nucleic acid fragment was treated with EcoRI, and it was then inserted into the EcoRI site of pUC-PaoxTaox to construct pUC-PaoxTaoxHIS4.

Subsequently, a nucleic acid fragment comprising the anti-β-galactosidase single-chain antibody gene (SEQ ID NO: 21) having a Mating Factor α prepro-signal sequence and BglII-recognizing sequences added to both sides of the gene was prepared by PCR using primers 13 (SEQ ID NO: 23) and 14 (SEQ ID NO: 24). The nucleic acid fragment was treated with BglII, and it was then inserted into the BglII site of pUC-PaoxTaoxHIS4 to construct pUC-PaoxscFvTaoxHIS4. This pUC-PaoxscFvTaoxHIS4 is designed, such that the anti-β-galactosidase single-chain antibody can be expressed under the control of the AOX1 promoter.

Production Example 3: Construction of Polypeptide PpMPP1-Expressing Vector

A gene fragment (SEQ ID NO: 25) having the multi-cloning site of HindIII-BamHI-SpeI-XbaI-EcoRI was totally synthesized, and the synthesized gene fragment was then inserted between the HindIII-EcoRI sites of pUC19 (manufactured by Takara Bio Inc., Code No. 3219), so as to construct pUC-2.

Moreover, a nucleic acid fragment comprising the GAP promoter (SEQ ID NO: 4) and BglII-recognizing sequences added to both sides of the promoter was prepared by PCR using primers 7 (SEQ ID NO: 13) and 8 (SEQ ID NO: 14). The nucleic acid fragment was treated with BamHI, and it was then inserted into the BamHI site of pUC-2 to construct pUC-Pgap.

Subsequently, a nucleic acid fragment comprising the promoter-regulated Zeocin (registered trademark) resistance gene (SEQ ID NO: 19) and EcoRI-recognizing sequences added to both sides of the gene was prepared by PCR using primers 15 (SEQ ID NO: 26) and 16 (SEQ ID NO: 27). The nucleic acid fragment was treated with EcoRI, and it was then inserted into the EcoRI site of pUC-Pgap to construct pUC-PgapZeo.

Subsequently, a nucleic acid fragment comprising the CCA38473 terminator (SEQ ID NO: 6) and XbaI-recognizing sequences added to both sides of the terminator was prepared by PCR using primers 11 (SEQ ID NO: 17) and 12 (SEQ ID NO: 18). The nucleic acid fragment was treated with XbaI, and it was then inserted into the XbaI site of pUC-PgapZeo to construct pUC-PgapT38473Zeo.

Subsequently, the nucleotide sequence (SEQ ID NO: 5) encoding the polypeptide PpMPP1 was prepared by PCR using primer 9 (SEQ ID NO: 15) and primer 10 (SEQ ID NO: 16). In each of these nucleic acid fragments, a GAP promoter sequence was added as an overlapping region upstream of the nucleotide sequence encoding the polypeptide PpMPP1, whereas a CCA38473 terminator sequence was added as an overlapping region downstream thereof.

pUC-PgapT38473Zeo was treated with SpeI, and then subjected to a PCR using the Re primer of the GAP promoter (primer 17 (SEQ ID NO: 28)) and the Fw primer of the CCA38473 terminator (primer 18 (SEQ ID NO: 29)) to prepare a nucleic acid fragment. The prepared nucleic acid fragment was mixed with the nucleic acid fragment encoding the polypeptide PpMPP1, which had been prepared by the above PCR, and the two fragments were then connected with each other using the Gibson Assembly System of New England Biolabs, so as to construct pUC-PgapPpMPP1T38473Zeo. This vector is designed, such that the polypeptide PpMPP1 having the amino acid sequence as set forth in SEQ ID NO: 30 can be expressed under the control of the GAP promoter.

Production Example 4: Construction of Vector for Inactivating Gene Consisting of Nucleotide Sequence as Set Forth in SEQ ID NO: 34

A gene fragment comprising the promoter-regulated G418 resistance gene (SEQ ID NO: 20) and homologous regions for transformation added to both sides of the gene was prepared by PCR using primer 19 (SEQ ID NO: 31) and primer 20 (SEQ ID NO: 32).

This vector comprises the promoter-regulated G418 resistance gene and homologous regions added to both sides of the gene. One of the homologous regions comprises a nucleotide sequence having a sequence identity of 100% to the nucleotide sequence of the promoter consisting of 97 nucleotides of the gene as set forth in SEQ ID NO: 34 encoding the amino acid sequence as set forth in SEQ ID NO: 33 (ACCESSION No. CCA41122) located upstream of the gene in the chromosome of *Komagataella pastoris* ATCC76273 strain. The other one of the homologous regions comprises a nucleotide sequence having a sequence identity of 100% to the nucleotide sequence of the terminator consisting of 98 nucleotides of the gene located downstream of the gene in the chromosome. Transforming a host cell with this vector inactivates the gene consisting of the nucleotide sequence as set forth in SEQ ID NO: 34.

Production Example 5: Construction of Vectors for Inactivating AOX1 Gene, FLD1 Gene, DAS1 Gene, and DAS2 Gene A gene fragment comprising the promoter-regulated Zeocin (registered trademark) resistance gene (SEQ ID NO: 19) and homologous regions for transformation added to both sides of the gene was prepared by PCR using primer 21 (SEQ ID NO: 35) and primer 22 (SEQ ID NO: 36).

This vector comprises the promoter-regulated Zeocin (registered trademark) resistance gene and homologous regions added to both sides of the gene. One of the homologous regions comprises a nucleotide sequence in the reading frames of the gene as set forth in SEQ ID NO: 37 encoding the AOX1 (ACCESSION No. CCA40305) of *Komagataella pastoris* ATCC76273 strain. The other of the homologous regions also comprises a nucleotide sequence in the reading frames of the same gene. Transforming a host cell with this vector inactivates the gene encoding AOX1.

A gene fragment comprising the promoter-regulated Zeocin (registered trademark) resistance gene (SEQ ID NO: 19) and homologous regions for transformation added to both sides of the gene was prepared by PCR using primer 23 (SEQ ID NO: 38) and primer 24 (SEQ ID NO: 39).

This vector comprises the promoter-regulated Zeocin (registered trademark) resistance gene and homologous regions added to both sides of the gene. One of the homologous regions comprises a nucleotide sequence consisting of 94 nucleotides located upstream of the gene as set forth in SEQ ID NO: 40 encoding the FLD1 (ACCESSION No. CCA39112) of *Komagataella pastoris* ATCC76273 strain in the chromosome of the strain. The other one of homologous regions comprises a nucleotide sequence consisting of 94 nucleotides located downstream of the same gene in the chromosome. Transforming a host cell with this vector inactivates the gene encoding FLD1.

A gene fragment comprising the promoter-regulated Zeocin (registered trademark) resistance gene (SEQ ID NO: 19) and homologous regions for transformation added to both sides of the gene was prepared by PCR using primer 25 (SEQ ID NO: 41) and primer 26 (SEQ ID NO: 42).

This vector comprises the promoter-regulated Zeocin (registered trademark) resistance gene and homologous regions added to both sides of the gene. One of the homologous regions comprises a nucleotide sequence consisting of 80 nucleotides located upstream of the gene as set forth in SEQ ID NO: 43 encoding the DAS1 (ACCESSION No. CCA39320) of *Komagataella pastoris* ATCC76273 strain in the chromosome of the strain. The other one of homologous regions comprises a nucleotide sequence consisting of 78 nucleotides located downstream of the same gene in the chromosome. Transforming a host cell with this vector inactivates the gene encoding DAS1.

A gene fragment comprising the promoter-regulated G418 resistance gene (SEQ ID NO: 20) and homologous regions for transformation added to both sides of the gene was prepared by PCR using primer 27 (SEQ ID NO: 44) and primer 28 (SEQ ID NO: 45).

This vector comprises the promoter-regulated G418 resistance gene and homologous regions added to both sides of the gene. One of the homologous regions comprises a nucleotide sequence consisting of 80 nucleotides located upstream of the gene as set forth in SEQ ID NO: 46 encoding the DAS2 (ACCESSION No. CCA39318) of *Komagataella pastoris* ATCC76273 strain in the chromosome of the strain. The other one of homologous regions comprises a nucleotide sequence consisting of 77 nucleotides located downstream of the same gene in the chromosome. Transforming a host cell with this vector inactivates the gene encoding DAS2.

Comparative Example 1: Preparation of Transformed Yeast

Using the anti-β-galactosidase single-chain antibody expressing vector pUC-PaoxscFvTaoxHIS4 constructed in Production Example 2, *Komagataella pastoris* was transformed as follows.

A histidine auxotrophic strain derived from the *Komagataella pastoris* ATCC76273 strain was inoculated into 3 ml of YPD medium (1% yeast extract bacto (manufactured by Becton Dickinson), 2% polypeptone (manufactured by NIHON PHARMACEUTICAL CO., LTD.), and 2% glucose), and the obtained mixture was then subjected to shaking culture overnight at 30° C., so as to obtain a pre-culture suspension. The obtained pre-culture suspension (500 μl) was inoculated into 50 ml of YPD medium, and the obtained mixture was then subjected to shaking culture until OD600 became 1 to 1.5. Thereafter, the cells were harvested (3000×g, 10 minutes, 20° C.), and were then re-suspended in 10 ml of 50 mM potassium phosphate buffer (pH 7.5) containing 250 μl of 1 M DTT (final concentration: 25 mM).

This suspension was incubated at 30° C. for 15 minutes, and the cells were harvested (3000×g, 10 minutes, 20° C.), and were then washed with 50 ml of STM buffer (270 mM sucrose, 10 mM Tris-HCl, and 1 mM magnesium chloride; pH 7.5) that had previously been cooled on ice. The cells were harvested from the washing buffer (3000×g, 10 minutes, 4° C.), and were then washed with 25 ml of STM buffer again. Thereafter, the cells were harvested (3000×g, 10 minutes, 4° C.). Finally, the cells were suspended in 250 μl of STM buffer cooled on ice, to obtain a competent cell suspension.

*Escherichia coli* was transformed using the anti-β-galactosidase single-chain antibody expressing vector pUC-PaoxscFvTaoxHIS4 constructed in Production Example 2, and the obtained transformant was then cultured in 2YT medium containing 5 ml of ampicillin (1.6% tryptone bacto (manufactured by Becton Dickinson), 1% yeast extract bacto (manufactured by Becton Dickinson), 0.5% sodium chloride, and 0.01% ampicillin sodium (manufactured by Wako Pure Chemical Industries, Ltd.)). Thereafter, using FastGene Plasmid Mini Kit (manufactured by NIPPON Genetics Co., Ltd.), pUC-PaoxscFvTaoxHIS4 was obtained from the cell mass. This plasmid was linearized by performing a SacI treatment, digesting a SacI-recognizing sequence in the AOX1 promoter.

This competent cell suspension (60 μl) was mixed with the linearized pUC-PaoxscFvTaoxHIS4 solution (1 μl), and the mixture was then transferred into a cuvette for electroporation (disposable cuvette electrode; electrode interval: 2 mm (manufactured by BM Equipment Co., Ltd.)), followed by subjecting it to 7.5 kV/cm, 25 μF, and 200Ω. After that, the cell mass was suspended in 1 ml of YPD medium, and the suspension was then left at rest at 30° C. for 1 hour. After the suspension had been left at rest for 1 hour, the cells were harvested (3000×g, 5 minutes, 20° C.), and were then suspended in 1 ml of YNB medium (0.67% yeast nitrogen base Without Amino Acid (manufactured by Becton Dickinson)). Thereafter, the cells were harvested again (3000×g, 5 minutes, 20° C.). The cell mass was re-suspended in a suitable amount of YNB medium, and the obtained suspension was then applied onto a YNB-selective agar plate (0.67% yeast nitrogen base Without Amino Acid (manufactured by Becton Dickinson), 1.5% agarose, and 2% glucose). Thereafter, a strain growing in a static culture at 30° C. for 3 days was collected. As a result, an anti-β-galactosidase single-chain antibody expressing yeast was obtained.

Example 1: Preparation of Transformed Yeast

Using the vector for inactivating the gene consisting of the nucleotide sequence as set forth in SEQ ID NO: 34 constructed in Production Example 4, the anti-β-galactosidase single-chain antibody expressing yeast was transformed as follows.

The anti-β-galactosidase single-chain antibody expressing yeast obtained in Comparative Example 1 was inoculated into 3 ml of YPD medium (1% yeast extract bacto (manufactured by Becton Dickinson), 2% polypeptone (manufactured by NIHON PHARMACEUTICAL CO., LTD.), and 2% glucose), and the obtained mixture was then subjected to shaking culture overnight at 30° C., so as to obtain a pre-culture suspension. The obtained pre-culture suspension (500 μl) was inoculated into 50 ml of YPD medium, and the obtained mixture was then subjected to shaking culture until OD600 became 1 to 1.5. Thereafter, the cells were harvested (3000×g, 10 minutes, 20° C.), and were then re-suspended in 10 ml of 50 mM potassium phosphate buffer (pH 7.5) containing 250 μl of 1 M DTT (final concentration: 25 mM).

This suspension was incubated at 30° C. for 15 minutes, and the cells were harvested (3000×g, 10 minutes, 20° C.), and were then washed with 50 ml of STM buffer (270 mM sucrose, 10 mM Tris-HCl, and 1 mM magnesium chloride; pH 7.5) that had previously been cooled on ice. The cells were harvested from the washing buffer (3000×g, 10 minutes, 4° C.), and were then washed with 25 ml of STM buffer again. Thereafter, the cells were harvested (3000×g, 10 minutes, 4° C.). Finally, the cells were suspended in 250 μl of STM buffer cooled on ice, to obtain a competent cell suspension.

This competent cell suspension (60 μl) was mixed with the vector (3 μl) for inactivating the gene consisting of the nucleotide sequence as set forth in SEQ ID NO: 34, which had been constructed in Production Example 4, and the mixture was then transferred into a cuvette for electroporation (disposable cuvette electrode; electrode interval: 2 mm (manufactured by BM Equipment Co., Ltd.)), followed by subjecting it to 7.5 kV/cm, 25 μF, and 200Ω. After that, the cell mass was suspended in 1 ml of YPD medium, and the suspension was then left at rest at 30° C. for 1 hour. After the suspension had been left at rest for 1 hour, the cells were harvested (3000×g, 5 minutes, 20° C.), and 950 μl of the supernatant was discarded. The cells were re-suspended in the remaining buffer, and the obtained suspension was then applied onto a YPD G418-selective agar plate (1% yeast extract (manufactured by Becton Dickinson), 2% polypeptone (manufactured by NIHON PHARMACEUTICAL CO., LTD.), 2% glucose, 1.5% agarose, and 0.05% G418 disulfate (manufactured by Nacalai Tesque, Inc.)). Thereafter, a strain growing in a static culture at 30° C. for 3 days was collected. As a result, an anti-β-galactosidase single-chain antibody expressing yeast, in which the gene consisting of the nucleotide sequence as set forth in SEQ ID NO: 34 was inactivated, was obtained.

Subsequently, using the polypeptide PpMPP1-expressing vector pUC-PgapPpMPP1T38473Zeo constructed in Production Example 3, the anti-β-galactosidase single-chain antibody expressing yeast, in which the gene consisting of the nucleotide sequence as set forth in SEQ ID NO: 34 was inactivated, was transformed as follows.

The anti-β-galactosidase single-chain antibody expressing yeast, in which the gene consisting of the nucleotide sequence as set forth in SEQ ID NO: 34 was inactivated, was inoculated into 3 ml of YPD medium (1% yeast extract bacto (manufactured by Becton Dickinson), 2% polypeptone (manufactured by NIHON PHARMACEUTICAL CO., LTD.), and 2% glucose), and the obtained mixture was then subjected to shaking culture overnight at 30° C., so as to obtain a pre-culture suspension. The obtained pre-culture suspension (500 μl) was inoculated into 50 ml of YPD medium, and the obtained mixture was then subjected to shaking culture until OD600 became 1 to 1.5. Thereafter, the cells were harvested (3000×g, 10 minutes, 20° C.), and were then re-suspended in 10 ml of 50 mM potassium phosphate buffer (pH 7.5) containing 250 μl of 1 M DTT (final concentration: 25 mM).

This suspension was incubated at 30° C. for 15 minutes, and the cells were harvested (3000×g, 10 minutes, 20° C.), and were then washed with 50 ml of STM buffer (270 mM sucrose, 10 mM Tris-HCl, and 1 mM magnesium chloride; pH 7.5) that had previously been cooled on ice. The cells were harvested from the washing buffer (3000×g, 10 minutes, 4° C.), and were then washed with 25 ml of STM buffer again. Thereafter, the cells were harvested (3000×g, 10 minutes, 4° C.). Finally, the cells were suspended in 250 μl of STM buffer cooled on ice, to obtain a competent cell suspension.

*Escherichia coli* was transformed using the polypeptide PpMPP1-expressing vector pUC-PgapPpMPP1T38473Zeo constructed in Production Example 3, and the obtained transformant was then cultured in 2YT medium containing 5 ml of ampicillin (1.6% tryptone bacto (manufactured by Becton Dickinson), 1% yeast extract bacto (manufactured by Becton Dickinson), 0.5% sodium chloride, and 0.01% ampicillin sodium (manufactured by Wako Pure Chemical Industries, Ltd.)). Thereafter, using FastGene Plasmid Mini Kit (manufactured by NIPPON Genetics Co., Ltd.), pUC-PgapPpMPP1T38473Zeo was obtained from the cell mass. This plasmid was linearized by performing a NruI treatment, digesting a NruI-recognizing sequence in the CCA38473 terminator.

This competent cell suspension (60 μl) was mixed with the linearized pUC-PgapPpMPP1T38473Zeo solution (1 μl), and the mixture was then transferred into a cuvette for electroporation (disposable cuvette electrode; electrode interval: 2 mm (manufactured by BM Equipment Co., Ltd.)), followed by subjecting it to 7.5 kV/cm, 25 μF, and 200Ω. After that, the cell mass was suspended in 1 ml of YPD medium, and the suspension was then left at rest at 30° C. for 1 hour. After the suspension had been left at rest for 1 hour, the cells were harvested (3000×g, 5 minutes, 20° C.), and 950 μl of the supernatant was discarded. The cells were re-suspended in the remaining buffer, and the obtained suspension was then applied onto a YPD G418-selective agar plate (1% yeast extract (manufactured by Becton Dickinson), 2% polypeptone (manufactured by NIHON PHARMACEUTICAL CO., LTD.), 2% glucose, 1.5% agarose, 0.05% G418 disulfate (manufactured by Nacalai Tesque, Inc.), and 0.01% Zeocin (trademark) (manufactured by Thermo Fisher Scientific)). Thereafter, a strain growing in a static culture at 30° C. for 3 days was collected. As a result, an anti-β-galactosidase single-chain antibody expressing yeast, in which the polypeptide PpMPP1 was expressed and the gene consisting of the nucleotide sequence as set forth in SEQ ID NO: 34 was inactivated, was obtained.

Comparative Example 2: Preparation of Transformed Yeast

Using the vectors for inactivating the AOX1 gene, the FLD1 gene and the DAS1 gene constructed in Production Example 5, the anti-β-galactosidase single-chain antibody expressing yeast was transformed as follows.

The anti-β-galactosidase single-chain antibody expressing yeast obtained in Comparative Example 1 was inoculated into 3 ml of YPD medium (1% yeast extract bacto (manufactured by Becton Dickinson), 2% polypeptone (manufactured by NIHON PHARMACEUTICAL CO., LTD.), and 2% glucose), and the obtained mixture was then subjected to shaking culture overnight at 30° C., so as to obtain a pre-culture suspension. The obtained pre-culture suspension (500 μl) was inoculated into 50 ml of YPD medium, and the obtained mixture was then subjected to shaking culture until OD600 became 1 to 1.5. Thereafter, the cells were harvested (3000×g, 10 minutes, 20° C.), and were then re-suspended in 10 ml of 50 mM potassium phosphate buffer (pH 7.5) containing 250 μl of 1 M DTT (final concentration: 25 mM).

This suspension was incubated at 30° C. for 15 minutes, and the cells were harvested (3000×g, 10 minutes, 20° C.), and were then washed with 50 ml of STM buffer (270 mM sucrose, 10 mM Tris-HCl, and 1 mM magnesium chloride; pH 7.5) that had previously been cooled on ice. The cells were harvested from the washing buffer (3000×g, 10 minutes, 4° C.), and were then washed with 25 ml of STM buffer again. Thereafter, the cells were harvested (3000×g, 10 minutes, 4° C.). Finally, the cells were suspended in 250 µl of STM buffer cooled on ice, to obtain a competent cell suspension.

This competent cell suspension (60 µl) was mixed with each of the vectors (3 µl) for inactivating the AOX1 gene, the FLD1 gene and the DAS1 gene, which had been constructed in Production Example 5, and the mixture was then transferred into a cuvette for electroporation (disposable cuvette electrode; electrode interval: 2 mm (manufactured by BM Equipment Co., Ltd.)), followed by subjecting it to 7.5 kV/cm, 25 µF, and 200Ω. After that, the cell mass was suspended in 1 ml of YPD medium, and the suspension was then left at rest at 30° C. for 1 hour. After the suspension had been left at rest for 1 hour, the cells were harvested (3000×g, 5 minutes, 20° C.), and 950 µl of the supernatant was discarded. The cells were re-suspended in the remaining buffer, and the obtained suspension was then applied onto a YPD Zeocin (trademark)-selective agar plate (1% yeast extract (manufactured by Becton Dickinson), 2% polypeptone (manufactured by NIHON PHARMACEUTICAL CO., LTD.), 2% glucose, 1.5% agarose, and 0.01% Zeocin (trademark) (manufactured by Thermo Fisher Scientific)). Thereafter, strains growing in a static culture at 30° C. for 3 days were collected. As a result, an anti-β-galactosidase single-chain antibody expressing yeast comprising an inactivated AOX1 gene, an anti-β-galactosidase single-chain antibody expressing yeast comprising an inactivated FLD1 gene, and an anti-β-galactosidase single-chain antibody expressing yeast comprising an inactivated DAS1 gene were obtained.

Subsequently, using the vector for inactivating the DAS2 gene constructed in Production Example 5, the anti-β-galactosidase single-chain antibody expressing yeast comprising an inactivated DAS1 gene was transformed as follows.

The anti-β-galactosidase single-chain antibody expressing yeast comprising an inactivated DAS1 gene was inoculated into 3 ml of YPD medium (1% yeast extract bacto (manufactured by Becton Dickinson), 2% polypeptone (manufactured by NIHON PHARMACEUTICAL CO., LTD.), and 2% glucose), and the obtained mixture was then subjected to shaking culture overnight at 30° C., so as to obtain a pre-culture suspension. The obtained pre-culture suspension (500 µl) was inoculated into 50 ml of YPD medium, and the obtained mixture was then subjected to shaking culture until OD600 became 1 to 1.5. Thereafter, the cells were harvested (3000×g, 10 minutes, 20° C.), and were then re-suspended in 10 ml of 50 mM potassium phosphate buffer (pH 7.5) containing 250 µl of 1 M DTT (final concentration: 25 mM).

This suspension was incubated at 30° C. for 15 minutes, and the cells were harvested (3000×g, 10 minutes, 20° C.), and were then washed with 50 ml of STM buffer (270 mM sucrose, 10 mM Tris-HCl, and 1 mM magnesium chloride; pH 7.5) that had previously been cooled on ice. The cells were harvested from the washing buffer (3000×g, 10 minutes, 4° C.), and were then washed with 25 ml of STM buffer again. Thereafter, the cells were harvested (3000×g, 10 minutes, 4° C.). Finally, the cells were suspended in 250 µl of STM buffer cooled on ice, to obtain a competent cell suspension.

This competent cell suspension (60 µl) was mixed with the vector (3 µl) for inactivating the DAS2 gene, which had been constructed in Production Example 5, and the mixture was then transferred into a cuvette for electroporation (disposable cuvette electrode; electrode interval: 2 mm (manufactured by BM Equipment Co., Ltd.)), followed by subjecting it to 7.5 kV/cm, 25 µF, and 200Ω. After that, the cell mass was suspended in 1 ml of YPD medium, and the suspension was then left at rest at 30° C. for 1 hour. After the suspension had been left at rest for 1 hour, the cells were harvested (3000×g, 5 minutes, 20° C.), and 950 µA of the supernatant was discarded. The cells were re-suspended in the remaining buffer, and the obtained suspension was then applied onto a YPD G418 Zeocin (trademark)-selective agar plate (1% yeast extract (manufactured by Becton Dickinson), 2% polypeptone (manufactured by NIHON PHARMACEUTICAL CO., LTD.), 2% glucose, 1.5% agarose, 0.05% G418 disulfate (manufactured by Nacalai Tesque, Inc.), and 0.01% Zeocin (trademark) (manufactured by Thermo Fisher Scientific)). Thereafter, a strain growing in a static culture at 30° C. for 3 days was collected. As a result, an anti-β-galactosidase single-chain antibody expressing yeast comprising an inactivated DAS1 gene and an inactivated DAS2 gene was obtained.

Example 2: Culture of Transformed Yeasts

The anti-β-galactosidase single-chain antibody expressing yeast, in which the gene consisting of the nucleotide sequence as set forth in SEQ ID NO: 34 was inactivated, and the anti-β-galactosidase single-chain antibody expressing yeast, in which the polypeptide PpMPP1 was expressed and the gene consisting of the nucleotide sequence as set forth in SEQ ID NO: 34 was inactivated, both of which had been obtained in Example 1, were each inoculated into 2 ml of BMMY medium (1% yeast extract bacto (manufactured by Becton Dickinson), 2% polypeptone (manufactured by NIHON PHARMACEUTICAL CO., LTD.), 0.34% yeast nitrogen base Without Amino Acid and Ammonium Sulfate (manufactured by Becton Dickinson), 1% Ammonium Sulfate, 0.4 mg/l Biotin, 100 mM potassium phosphate (pH 6.0), and 2% Methanol), and the obtained mixture was then subjected to shaking culture at 30° C., at 170 rpm, for 72 hours. Thereafter, the reaction mixture was centrifuged (12000 rpm, 5 minutes, 4° C.) to collect the culture supernatant. The concentration of the cell mass was measured by OD600.

Comparative Example 3: Culture of Transformed Yeasts

The anti-β-galactosidase single-chain antibody expressing yeast obtained in Comparative Example 1, and the anti-β-galactosidase single-chain antibody expressing yeast having an inactivated AOX1 gene, the anti-β-galactosidase single-chain antibody expressing yeast having an inactivated FLD1 gene, and the anti-β-galactosidase single-chain antibody expressing yeast having an inactivated DAS1 gene and an inactivated DAS2 gene, which were obtained in Comparative Example 2, were each cultured by the same method as that of the above-described Example 2. Thereafter, the reaction mixture was centrifuged (12000 rpm, 5 minutes, 4°

C.) to collect a culture supernatant. The concentration of the cell mass was measured by OD600.

Example 3: ELISA-Based Measurement of Produced Amount of Anti-β-Galactosidase Single-Chain Antibody The amount of the anti-β-galactosidase single-chain antibody produced in the culture supernatant obtained in Example 2 was measured by the following method according to a sandwich ELISA (Enzyme-Linked Immunosorbent Assay).

β-Galactosidase (5 mg/mL, manufactured by Roche), which was 2500 times diluted with an immobilization buffer (8 g/L sodium chloride, 0.2 g/L potassium chloride, 1.15 g/L sodium monohydrogen phosphate (anhydrous), 0.2 g/L potassium dihydrogen phosphate (anhydrous), and 1 mM magnesium chloride), was added in an amount of 50 µl each per well to an ELISA plate (Nunc Immuno Plate Maxisorp (manufactured by Thermo Fisher Scientific)), and it was then incubated overnight at 4° C. After completion of the incubation, the solution in the well was removed, and was then blocked with 200 µl of ImmunoBlock (manufactured by Sumitomo Dainippon Pharma Co., Ltd.), followed by leaving at rest at room temperature for 1 hour. The plate was washed with a PBST buffer (8 g/L sodium chloride, 0.2 g/L potassium chloride, 1.15 g/L sodium monohydrogen phosphate (anhydrous), 0.2 g/L potassium dihydrogen phosphate (anhydrous), and 0.1% Tween 20) three times. Thereafter, a serially diluted standard anti-β-galactosidase single-chain antibody and a diluted culture supernatant were added, in an amount of 50 µl each per well, to the plate, followed by performing a reaction at room temperature for 1 hour. The plate was then washed with the PBST buffer three times, and a secondary antibody solution (secondary antibody: Anti-His-tag mAb-HRP-DirecT (manufactured by MBL)), which was 8000 times diluted with the PBST buffer, was added in an amount of 50 µl per well, followed by performing a reaction at room temperature for 1 hour. The plate was then washed with the PBST buffer three times, and 50 µl of TMB-1 Component Microwell Peroxidase Substrate SureBlue (manufactured by KPL) was added thereto, followed by leaving at rest at room temperature for 20 minutes. Thereafter, 50 µl of TMB Stop Solution (manufactured by KPL) was added to the reaction mixture to terminate the reaction, and the absorbance at 450 nm was then measured using a microplate reader (Spectra Max Paradigm; manufactured by Molecular Devices). The amount of the anti-β-galactosidase single-chain antibody in the culture supernatant was quantified by using a calibration curve of the standard anti-β-galactosidase single-chain antibody. The produced amount of the anti-β-galactosidase single-chain antibody measured by this method and the concentration of each cell mass (OD600) are shown in Table 1.

Comparative Example 4: ELISA-Based Measurement of Produced Amount of Anti-β-Galactosidase Single-Chain Antibody The amount of the anti-β-galactosidase single-chain antibody produced in each of the culture supernatants obtained in Comparative Example 3 was also measured by the same method as that of Example 3. The produced amount of the anti-β-galactosidase single-chain antibody measured by this method and the concentration of each cell mass (OD600) are shown in Table 1.

<Results>

TABLE 1

| Transformed yeast | mg/L | OD600 |
|---|---|---|
| 1. Anti-β-galactosidase single-chain antibody expressing yeast (Comparative Example 1) | 23.8 | 36.5 |
| 2. Anti-β-galactosidase single-chain antibody expressing yeast in which gene consisting of nucleotide sequence as set forth in SEQ ID NO: 34 is inactivated (Example 1) | 39.1 | 10.6 |
| 3. Anti-β-galactosidase single-chain antibody expressing yeast having inactivated AOX1 gene (Comparative Example 2) | 13.7 | 9.9 |
| 4. Anti-β-galactosidase single-chain antibody expressing yeast having inactivated FLD1 gene (Comparative Example 2) | 2.3 | 8.8 |
| 5. Anti-β-galactosidase single-chain antibody expressing yeast having inactivated DAS1 gene and inactivated DAS2 gene (Comparative Example 2) | 2.2 | 9.0 |
| 6. Anti-β-galactosidase single-chain antibody expressing yeast in which polypeptide PpMPP1 is expressed and gene consisting of nucleotide sequence as set forth in SEQ ID NO: 34 is inactivated (Example 1) | 164.1 | 7.0 |
| 6. Anti-β-galactosidase single-chain antibody expressing yeast in which polypeptide PpMPP1 is expressed and gene consisting of nucleotide sequence as set forth in SEQ ID NO: 34 is inactivated (Example 1) | 164.1 | 7.0 |
| 7. Anti-β-galactosidase single-chain antibody expressing yeast in which polypeptide PpMPP1 is expressed (Comparative Example 2) | 48.8 | 26.7 |

As shown in Table 1, the anti-β-galactosidase single-chain antibody expressing yeast (2) obtained in Example 1, in which the gene consisting of the nucleotide sequence as set forth in SEQ ID NO: 34 was inactivated, apparently had a reduced ability to utilize methanol in comparison to that of the anti-β-galactosidase single-chain antibody expressing yeast (1) obtained in Comparative Example 1, and exhibited a higher productivity of the antibody. In addition, the anti-β-galactosidase single-chain antibody expressing yeast (2) obtained in Example 1, in which the gene consisting of the nucleotide sequence as set forth in SEQ ID NO: 34 was inactivated, had a reduced ability to utilize methanol at the same level as the anti-β-galactosidase single-chain antibody expressing yeast (3) having an inactivated AOX1 gene, the anti-β-galactosidase single-chain antibody expressing yeast (4) having an inactivated FLD1 gene, and the anti-β-galactosidase single-chain antibody expressing yeast (5) having an inactivated DAS1 gene and an inactivated DAS2 gene, which were constructed in Comparative Example 2 with the intention of reducing the ability. The anti-β-galactosidase single-chain antibody expressing yeast (2) obtained in Example 1 apparently exhibited a higher productivity of the antibody than the anti-β-galactosidase single-chain antibody expressing yeasts (3), (4) and (5). These results demonstrate that methanol was efficiently utilized as a carbon source for the target protein as a result of inactivation of the gene consisting of the nucleotide sequence as set forth in SEQ ID NO: 34.

Moreover, the anti-β-galactosidase single-chain antibody expressing yeast (6) obtained in Example 1, in which the polypeptide PpMPP1 was expressed and the gene consisting of the nucleotide sequence as set forth in SEQ ID NO: 34 was inactivated, had a lower ability to utilize methanol and exhibited a higher productivity of the antibody, than the anti-β-galactosidase single-chain antibody expressing yeast (1) obtained in Comparative Example 1. In addition, the anti-β-galactosidase single-chain antibody expressing yeast (6) obtained in Example 1, in which the polypeptide PpMPP1 was expressed and the gene consisting of the nucleotide sequence as set forth in SEQ ID NO: 34 was inactivated, exhibited a further higher productivity of the antibody, than the anti-β-galactosidase single-chain antibody expressing yeast (2) obtained in Example 1, in which the gene consisting of the nucleotide sequence as set forth in SEQ ID NO: 34 was inactivated. These results suggest that the combination of expressing the polypeptide PpMPP1 and inactivating the gene consisting of the nucleotide sequence as set forth in SEQ ID NO: 34 further reduced the ability to utilize methanol and further increased the productivity of the antibody.

All publications, patents and patent applications cited in the present description are incorporated herein by reference in their entirety.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

What is claimed is:

1. A host cell comprising an inactivated gene, wherein the inactivated gene is selected from the group consisting of:
   a gene comprising the nucleotide sequence of SEQ ID NO: 34;
   a gene comprising a nucleotide sequence having a sequence identity of 95% or more to the nucleotide sequence of SEQ ID NO: 34,
   wherein the gene comprising the nucleotide sequence having a sequence identity of 95% or more to the nucleotide sequence of SEQ ID NO: 34 retains the function of the gene comprising the nucleotide sequence of SEQ ID NO: 34, which is encoding the amino acid sequence set forth in SEQ ID NO: 33 and variants thereof, in the host cell; and
   a gene encoding an amino acid sequence having a sequence identity of 95% or more to the amino acid sequence of SEQ ID NO: 33,
   wherein the gene encoding an amino acid sequence having a sequence identity of 95% or more to the amino acid sequence of SEQ ID NO: 33 retains the function of the gene comprising the nucleotide sequence of SEQ ID NO: 34, which is encoding the amino acid sequence set forth in SEQ ID NO: 33 and variants thereof, in the host cell,
   wherein upon gene inactivation the host cell has a reduced ability to utilize methanol compared to a parent cell,
   wherein the host cell is a methanol-utilizing yeast belonging to the genus *Komagataella*, and
   wherein the host cell is obtained by transforming a parent cell with a first vector comprising a nucleotide sequence encoding a target protein.

2. The host cell according to claim 1, wherein the first vector further comprises:
   a nucleotide sequence having a region homologous to the inactivated gene, wherein the region has 95% or more sequence identity to a corresponding region in the inactivated gene, and wherein the nucleotide sequence is incorporated into the chromosome of the host cell through homologous recombination;

a nucleotide sequence having a region homologous to a promoter of the inactivated gene, wherein the region has 95% or more sequence identity to a corresponding region in the promoter, and wherein the nucleotide sequence is incorporated into the chromosome of the host cell through homologous recombination; and/or a nucleotide sequence having a region homologous to a terminator of the inactivated gene, wherein the region has 95% or more sequence identity to a corresponding region in the terminator, and wherein the nucleotide sequence is incorporated into the chromosome of the host cell through homologous recombination.

3. The host cell according to claim 1 wherein the host cell is obtained by transforming the parent cell with a second vector, and wherein the second vector comprises:

a nucleotide sequence having a region homologous to the inactivated gene, wherein the region has 95% or more sequence identity to a corresponding region in the inactivated gene, and wherein the nucleotide sequence is incorporated into the chromosome of the host cell through homologous recombination;

a nucleotide sequence having a region homologous to a promoter of the inactivated gene, wherein the region has 95% or more sequence identity to a corresponding region in the promoter, and wherein the nucleotide sequence is incorporated into the chromosome of the host cell through homologous recombination; and/or a nucleotide sequence having a region homologous to a terminator of the inactivated gene, wherein the region has 95% or more sequence identity to a corresponding region in the terminator, and wherein the nucleotide sequence is incorporated into the chromosome of the host cell through homologous recombination.

4. The host cell according to claim 1, wherein the host cell is obtained by transforming the parent cell with an additional vector, and wherein the additional vector comprises a nucleotide sequence selected from the group consisting of:

a nucleotide sequence encoding the amino acid sequence of SEQ ID NO: 30;

a nucleotide sequence encoding a first variant amino acid sequence of SEQ ID NO: 30 comprising 1 to 50 amino acid substitutions, deletions, and/or additions in the amino acid sequence of SEQ ID NO: 30, wherein the first variant amino acid sequence retains the function of the amino acid sequence of SEQ ID NO: 30, which is a transcriptional factor for activating a methanol-inducible promoter; and a nucleotide sequence encoding a second variant amino acid sequence having a sequence identity of 95% or more to the amino acid sequence of SEQ ID NO: 30, wherein the second variant amino acid sequence retains the function of the amino acid sequence of SEQ ID NO: 30, which is a transcriptional factor for activating a methanol-inducible promoter.

5. A method for producing a target protein, comprising:

culturing the host cell according to claim 1; and collecting the target protein from a culture mixture.

6. The method according to claim 5, wherein the target protein is a heterologous protein.

7. The method according to claim 5, wherein the culturing is performed in a culture mixture comprising one or more carbon sources selected from the group consisting of glucose, glycerol, and methanol.

\* \* \* \* \*

```
                    SEQUENCE LISTING

<160> NUMBER OF SEQ ID NOS: 46

<210> SEQ ID NO 1
<211> LENGTH: 933
<212> TYPE: DNA
<213> ORGANISM: Komagataella pastoris

<400> SEQUENCE: 1
aacatccaaa gacgaaaggt tgaatgaaac cttttttgcca tccgacatcc acaggtccat      60
tctcacacat aagtgccaaa cgcaacagga ggggatacac tagcagcaga ccgttgcaaa     120
cgcaggacct ccactcctct tctcctcaac acccactttt gccatcgaaa aaccagccca     180
gttattgggc ttgattggag ctcgctcatt ccaattcctt ctattaggct actaacacca     240
tgactttatt agcctgtcta tcctggcccc cctggcgagg ttcatgtttg tttatttccg     300
aatgcaacaa gctccgcatt acacccgaac atcactccag atgagggctt tctgagtgtg     360
gggtcaaata gtttcatgtt ccccaaatgg cccaaaactg acagtttaaa cgctgtcttg     420
gaacctaata tgacaaaagc gtgatctcat ccaagatgaa ctaagtttgg ttcgttgaaa     480
tgctaacggc cagttggtca aaaagaaact tccaaaagtc ggcataccgt ttgtcttgtt     540
tggtattgat tgacgaatgc tcaaaaataa tctcattaat gcttagcgca gtctctctat     600
cgcttctgaa ccccggtgca cctgtgccga aacgcaaatg gggaaacacc cgcttttttgg     660 atgattatgc attgtctcca cattgtatgc ttccaagatt ctggtgggaa tactgctgat     720
agcctaacgt tcatgatcaa aatttaactg ttctaacccc tacttgacag caatatataa     780
acagaaggaa gctgccctgt cttaaacctt ttttttatca tcattattag cttactttca     840
taattgcgac tggttccaat tgacaagctt ttgattttaa cgactttaaa cgacaacttg     900
agaagatcaa aaaacaacta attattcgaa acg                                   933

<210> SEQ ID NO 2
<211> LENGTH: 499
<212> TYPE: DNA
<213> ORGANISM: Komagataella pastoris

<400> SEQUENCE: 2
tcaagaggat gtcagaatgc catttgcctg agagatgcag gcttcatttt tgatactttt      60
ttatttgtaa cctatatagt ataggatttt ttttgtcatt ttgtttcttc tcgtacgagc     120
ttgctcctga tcagcctatc tcgcagctga tgaatatctt gtggtagggg tttgggaaaa     180
tcattcgagt ttgatgtttt tcttggtatt tcccactcct cttcagagta cagaagatta     240
```

| | |
|---|---|
| agtgagacgt tcgtttgtgc aagcttcaac gatgccaaaa gggtataata agcgtcattt | 300 |
| gcagcattgt gaagaaaact atgtggcaag ccaagcctgc gaagaatgta ttttaagttt | 360 |
| gactttgatg tattcacttg attaagccat aattctcgag tatctatgat tggaagtatg | 420 |
| ggaatggtga tacccgcatt cttcagtgtc ttgaggtctc ctatcagatt atgcccaact | 480 |
| aaagcaaccg gaggaggag | 499 |

<210> SEQ ID NO 3
<211> LENGTH: 2656
<212> TYPE: DNA
<213> ORGANISM: Komagataella pastoris

<400> SEQUENCE: 3

| | |
|---|---|
| agatctcctg atgactgact cactgataat aaaaatacgg cttcagaatt tctcaagact | 60 |
| acactcactg tccgacttca agtatgacat ttcccttgct acctgcatac gcaagtgttg | 120 |
| cagagtttga taattccttg agtttggtag gaaaagccgt gtttccctat gctgctgacc | 180 |
| agctgcacaa cctgatcaag ttcactcaat cgactgagct tcaagttaat gtgcaagttg | 240 |
| agtcatccgt tacagaggac caatttgagg agctgatcga caacttgctc aagttgtaca | 300 |
| ataatggtat caatgaagtg attttggacc tagatttggc agaaagagtt gtccaaagga | 360 |
| tcccaggcgc tagggttatc tataggaccc tggttgataa agttgcatcc ttgcccgcta | 420 |
| atgctagtat cgctgtgcct ttttcttctc cactgggcga tttgaaaagt ttcactaatg | 480 |
| gcggtagtag aactgtttat gcttttttctg agaccgcaaa gttggtagat gtgacttcca | 540 |
| ctgttgcttc tggtataatc cccattattg atgctcggca attgactact gaatacgaac | 600 |
| tttctgaaga tgtcaaaaag ttccctgtca gtgaaatttt gttggcgtct tgactactg | 660 |
| accgccccga tggtctattc actactttgg tggctgactc ttctaattac tcgttgggcc | 720 |
| tggtgtactc gtccaaaaag tctattccgg aggctataag gacacaaact ggagtctacc | 780 |
| aatctcgtcg tcacggtttg tggtataaag gtgctcatc tggagcaact caaaagttgc | 840 |
| tgggtatcga attggattgt gatggagact gcttgaaatt tgtggttgaa caaacaggtg | 900 |
| ttggtttctg tcacttggaa cgcacttcct gttttggcca atcaaagggt cttagagcca | 960 |
| tggaagccac cttgtgggat cgtaagagca atgctccaga aggttcttat accaaacggt | 1020 |
| tatttgacga cgaagttttg ttgaacgcta aaattaggga ggaagctgat gaacttgcag | 1080 |
| aagctaaatc caaggaagat atagcctggg aatgtgctga cttatttat tttgcattag | 1140 |
| ttagatgtgc caagtacggt gtgacgttgg acgaggtgga gagaaacctg gatatgaagt | 1200 |
| ccctaaaggt cactagaagg aaaggagatg ccaagccagg atacaccaag gaacaaccta | 1260 |
| aagaagaatc caaccctaaa gaagtccctt ctgaaggtcg tattgaattg tgcaaaattg | 1320 |
| acgtttctaa ggcctcctca caagaaattg aagatgccct tcgtcgtcct atccagaaaa | 1380 |
| cggaacagat tatggaatta gtcaaaccaa ttgtcgacaa tgttcgtcaa aatggtgaca | 1440 |
| aagcccttt agaactaact gccaagtttg atggagtcgc tttgaagaca cctgtgttag | 1500 |
| aagctccttt cccagaggaa cttatgcaat tgccagataa cgttaagaga gccattgatc | 1560 |
| tctctataga taacgtcagg aaattccatg aagctcaact aacggagacg ttgcaagttg | 1620 |
| agacttgccc tggtgtagtc tgctctcgtt ttgcaagacc tattgagaaa gttggcctct | 1680 |
| atattcctgg tggaaccgca attctgcctt ccacttccct gatgctgggt gttcctgcca | 1740 |
| aagttgctgt tgcaaagaa attgttttg catctccacc taagaaggat ggtacccta | 1800 |
| ccccagaagt catctacgtt gcccacaagg ttggtgctaa gtgtatcgtg ctagcaggag | 1860 |

```
gcgcccaggc agtagctgct atggcttacg aacagaaac  tgttcctaag tgtgacaaaa    1920
tatttggtcc aggaaccag  ttcgttactg ctgccaagat gatggttcaa aatgacacat    1980
cagccctgtg tagtattgac atgcctgctg ggccttctga agttctagtt attgctgata    2040
aatacgctga tccagatttc gttgcctcag accttctgtc tcaagctgaa catggtattg    2100
attcccaggt gattctgttg gctgtcgata tgacagacaa ggagcttgcc agaattgaag    2160
atgctgttca caaccaagct gtgcagttgc aagggttga  aattgtacgc aagtgtattg    2220
cacactctac aaccctatcg gttgcaacct acgagcaggc tttggaaatg tccaatcagt    2280
acgctcctga cacttgatc  ctgcaaatcg agaatgcttc ttcttatgtt gatcaagtac    2340
aacacgctgg atctgtgttt gttggtgcct actctccaga gagttgtgga gattactcct    2400
ccggtaccaa ccacactttg ccaacgtacg gatatgcccg tcaatacagc ggagttaaca    2460
ctgcaacctt ccagaagttc atcacttcac aagacgtaac tcctgaggga ctgaaacata    2520
ttggccaagc agtgatggat ctggctgctg ttgaaggtct agatgctcac cgcaatgctg    2580
ttaaggttcg tatggagaaa ctgggactta tttaattatt tagagatttt aacttacatt    2640
tagattcgat agatct                                                   2656

<210> SEQ ID NO 4
<211> LENGTH: 487
<212> TYPE: DNA
<213> ORGANISM: Komagataella pastoris

<400> SEQUENCE: 4 tttttttgtag aaatgtcttg gtgtcctcgt ccaatcaggt agccatctct gaaatatctg    60
gctccgttgc aactccgaac gacctgctgg caacgtaaaa ttctccgggg taaaacttaa   120
atgtggagta atggaaccag aaacgtctct tcccttctct ctccttccac cgcccgttac   180
cgtccctagg aaattttact ctgctggaga gcttcttcta cggccccctt gcagcaatgc   240
tcttcccagc attacgttgc gggtaaaacg gaggtcgtgt acccgaccta gcagcccagg   300
gatggaaaag tcccggccgt cgctggcaat aatagcgggc ggacgcatgt catgagatta   360
ttggaaacca ccagaatcga atataaaagg cgaacacctt tcccaatttt ggtttctcct   420
gacccaaaga ctttaaattt aatttatttg tccctatttc aatcaattga caactatca    480 aaacaca                                                             487

<210> SEQ ID NO 5
<211> LENGTH: 2667
<212> TYPE: DNA
<213> ORGANISM: Komagataella pastoris

<400> SEQUENCE: 5
atgagtaccg cagccccaat caaggaagaa agccaatttg cccatttgac cctaatgaac     60
aaggatatac cttcgaacgc aaaacaggca agtcgaaag  tttcagcggc ccctgctaag    120
acgggctcca aatctgctgg tggatctggc aacaacaacg ctgcacctgt gaaaaaaga    180 gtccgcacgg gctgtttgac ctgccgaaag aagcacaaga atgtgacga  aacagaaac    240 ccaaaatgtg acttttgcac tttgaaaggc ttgaatgtg  tctggccaga gaacaataag    300
aagaatatct tcgttaacaa ctccatgaag gatttcttag gcaagaaaac ggtggatgga    360
gctgatagtc tcaatttggc cgtgaatctg caacaacagc agagttcaaa cacaattgcc    420
aatcaatcgc tttcctcaat tggattggaa agttttggtt acggctctgg tatcaaaaac    480
```

```
gagtttaact tccaagactt gataggttca aactctggca gttcagatcc gacatttca      540 gtagacgctg acgaggccca aaaactcgac atttccaaca agaacagtcg taagagacag     600
aaactaggtt tgctgccggt cagcaatgca acttcccatt tgaacggttt caatggaatg     660
tccaatggaa agtcacactc tttctcttca ccgtctggga ctaatgacga tgaactaagt     720
ggcttgatgt tcaactcacc aagcttcaac ccctcacag ttaacgattc taccaacaac      780
agcaaccaca ataggtttt gtctccgatg tcatgcttat tttctacagt tcaagaagca      840
tctcaaaaaa agcatggaaa ttccagtaga cacttttcat acccatctgg gccggaggac     900
ctttggttca atgagttcca aaaacaggcc ctcacagcca atggagaaaa tgctgtccaa     960
cagggagatg atgcttctaa gaacaacaca gccattccta aggaccagtc ttcgaactca     1020
tcgattttca gttcacgttc tagtgcagct tctagcaact caggagacga tattggaagg    1080
atgggcccat tctccaaagg accagagatt gagttcaact acgattcttt tttggaatcg    1140
ttgaaggcag agtcaccctc ttcttcaaag tacaatctgc cggaaacttt gaaagagtac     1200 atgacccta gttcgtctca tctgaatagt caacactccg acactttggc aaatggcact     1260
aacggtaact attctagcac cgttccaac aacttgagct taagtttgaa ctccttctct       1320
ttctctgaca gttctcatt gagtccacca acaatcactg acgccgaaaa gttttcattg     1380
atgagaaact tcattgacaa catctcgcca tggtttgaca cttttgacaa taccaaacag    1440 tttgaacaa aaattccagt tctggccaaa aaatgttctt cattgtacta tgccattctg      1500
gctatatctt ctcgtcaaag agaaaggata agaaagagc acaatgaaaa aacattgcaa     1560
tgctaccaat actcactaca acagctcatc cctactgttc aaagctcaaa taatattgag     1620
tacattatca catgtattct cctgagtgtg ttccacatca tgtctagtga accttcaacc    1680
cagagggaca tcattgtgtc attggcaaaa tacattcaag catgcaacat aaacggattt    1740
acatctaatg acaaactgga aaagagtatt ttctggaact atgtcaattt ggatttggct     1800
acttgtgcaa tcggtgaaga gtcaatggtc attccttta gctactgggt taaagagaca     1860
actgactaca agaccattca agatgtgaag ccattttca ccaagaagac tagcacgaca     1920
actgacgatg acttggacga tatgtatgcc atctacatgc tgtacattag tggtagaatc    1980
attaacctgt tgaactgcag agatgcgaag ctcaattttg agcccaagtg ggagttttg    2040 tggaatgaac tcaatgaatg ggaattgaac aaacccttga cctttcaaag tattgttcag    2100
ttcaaggcca atgacgaatc gcagggcgga tcaactttc caactgttct attctccaac     2160
tctcgaagct gttacagtaa ccagctgtat catatgagct acatcatctt agtgcagaat    2220
aaaccacgat tatacaaaat cccctttact acagtttctg cttcaatgtc atctccatcg    2280
gacaacaaag ctgggatgtc tgcttccagc acacctgctt cagaccacca cgcttctggt    2340
gatcatttgt ctccaagaag tgtagagccc tctctttcga caacgttgag ccctccgcct    2400
aatgcaaacg gtgcaggtaa caagttccgc tctacgctct ggcatgccaa gcagatctgt    2460
gggatttcta tcaacaacaa ccacaacagc aatctagcag ccaaagtgaa ctcattgcaa    2520
ccattgtggc acgctggaaa gctaattagt tccaagtctg aacatacaca gttgctgaaa    2580
ctgttgaaca accttgagtg tgcaacaggc tggcctatga actggaaggg caaggagtta    2640
attgactact ggaatgttga agaatag                                        2667
```

<210> SEQ ID NO 6
<211> LENGTH: 600
<212> TYPE: DNA
<213> ORGANISM: Komagataella pastoris -continued

<400> SEQUENCE: 6

| | | | | | |
|---|---|---|---|---|---|
| gacaataaga | agaaaaaaaa | agaaaagcgg | tggggagggg | attattaaat | aaggattatg | 60 |
| taacccagg | gtaccgttct | atacatattt | aaggattatt | taggacaatc | gatgaaatcg | 120 |
| gcatcaaact | ggatgggagt | atagtgtccg | gataatcgga | taaatcatct | tgcgaggagc | 180 |
| cgcttggttg | gttggtgaga | ggagtgaaat | atgtgtctcc | tcacccaaga | atcgcgatat | 240 |
| cagcaccctg | tgggggacac | tattggcctc | cctcccaaac | cttcgatgtg | gtagtgcttt | 300 |
| attatattga | ttacattgat | tacatagcta | aaccctgcct | ggttgcaagt | tgagctccga | 360 |
| attccaatat | tagtaaaatg | cctgcaagat | aacctcggta | tggcgtccga | ccccgcttaa | 420 |
| ttattttaac | tcctttccaa | cgaggacttc | gtaattttg | attagggagt | tgagaaacgg | 480 |
| ggggtcttga | tacctcctcg | atttcagatc | ccaccccctc | tcagtcccaa | gtgggacccc | 540 |
| cctcggccgt | gaaatgcgcg | cactttagtt | tttttcgcat | gtaaacgccg | gtgtccgtca | 600 |

<210> SEQ ID NO 7
<211> LENGTH: 31
<212> TYPE: DNA
<213> ORGANISM: Artificial Sequence
<220> FEATURE:
<223> OTHER INFORMATION: primer1

<400> SEQUENCE: 7
ttaggatcca acatccaaag acgaaaggtt g                              31

<210> SEQ ID NO 8
<211> LENGTH: 38
<212> TYPE: DNA
<213> ORGANISM: Artificial Sequence
<220> FEATURE:
<223> OTHER INFORMATION: primer2

<400> SEQUENCE: 8
ttaggatccc gtttcgaata attagttgtt ttttgatc                       38

<210> SEQ ID NO 9
<211> LENGTH: 39
<212> TYPE: DNA
<213> ORGANISM: Artificial Sequence
<220> FEATURE:
<223> OTHER INFORMATION: primer3

<400> SEQUENCE: 9
ttatctagat caagaggatg tcagaatgcc atttgcctg                      39

<210> SEQ ID NO 10
<211> LENGTH: 30
<212> TYPE: DNA
<213> ORGANISM: Artificial Sequence
<220> FEATURE:
<223> OTHER INFORMATION: primer4

<400> SEQUENCE: 10
ttatctagac tcctcctccg gttgctttag                                30

<210> SEQ ID NO 11
<211> LENGTH: 32
<212> TYPE: DNA
<213> ORGANISM: Artificial Sequence
<220> FEATURE:
<223> OTHER INFORMATION: primer5

<400> SEQUENCE: 11
ttagaattcg gatctcctga tgactgactc ac                                32

<210> SEQ ID NO 12
<211> LENGTH: 41
<212> TYPE: DNA
<213> ORGANISM: Artificial Sequence
<220> FEATURE:
<223> OTHER INFORMATION: primer6

<400> SEQUENCE: 12
ttagaattcg gatctatcga atctaaatgt aagttaaaat c                       41

<210> SEQ ID NO 13
<211> LENGTH: 30
<212> TYPE: DNA
<213> ORGANISM: Artificial Sequence
<220> FEATURE:
<223> OTHER INFORMATION: primer7

<400> SEQUENCE: 13
ttaggatcct ttttgtaga aatgtcttgg                                     30

<210> SEQ ID NO 14
<211> LENGTH: 37
<212> TYPE: DNA
<213> ORGANISM: Artificial Sequence
<220> FEATURE:
<223> OTHER INFORMATION: primer8

<400> SEQUENCE: 14
ttaggatcct gtgttttgat agttgttcaa ttgattg                            37

<210> SEQ ID NO 15
<211> LENGTH: 53
<212> TYPE: DNA
<213> ORGANISM: Artificial Sequence
<220> FEATURE:
<223> OTHER INFORMATION: primer9

<400> SEQUENCE: 15
caatcaattg aacaactatc aaaacacaat gagtaccgca gccccaatca agg          53

<210> SEQ ID NO 16
<211> LENGTH: 54
<212> TYPE: DNA
<213> ORGANISM: Artificial Sequence
<220> FEATURE:
<223> OTHER INFORMATION: primer10

<400> SEQUENCE: 16
ccgcttttct ttttttttct tcttattgtc ctattcttca acattccagt agtc         54

<210> SEQ ID NO 17
<211> LENGTH: 39
<212> TYPE: DNA
<213> ORGANISM: Artificial Sequence
<220> FEATURE:
<223> OTHER INFORMATION: primer11

<400> SEQUENCE: 17
ttatctagag acaataagaa gaaaaaaaaa gaaaagcgg                          39

<210> SEQ ID NO 18
<211> LENGTH: 29

```
<212> TYPE: DNA
<213> ORGANISM: Artificial Sequence
<220> FEATURE:
<223> OTHER INFORMATION: primer12

<400> SEQUENCE: 18
ttatctagat gacggacacc ggcgtttac                                29

<210> SEQ ID NO 19
<211> LENGTH: 855
<212> TYPE: DNA
<213> ORGANISM: Artificial Sequence
<220> FEATURE:
<223> OTHER INFORMATION: Zeo

<400> SEQUENCE: 19
cccacacacc atagcttcaa aatgtttcta ctcctttttt actcttccag attttctcgg    60
actccgcgca tcgccgtacc acttcaaaac acccaagcac agcatactaa attttccctc   120
tttcttcctc tagggtgtcg ttaattaccc gtactaaagg tttggaaaag aaaaaagaga   180
ccgcctcgtt tcttttttctt cgtcgaaaaa ggcaataaaa attttttatca cgtttctttt   240 tcttgaaatt ttttttttta gtttttttct ctttcagtga cctccattga tatttaagtt   300
aataaacggt cttcaatttc tcaagtttca gtttcatttt tcttgttcta ttacaacttt   360
ttttacttct tgttcattag aaagaaagca tagcaatcta atctaagggg cggtgttgac   420
aattaatcat cggcatagta tatcggcata gtataatacg acaaggtgag gaactaaacc   480
atggccaagt tgaccagtgc cgttccggtg ctcaccgcgc gcgacgtcgc cggagcggtc   540
gagttctgga ccgaccggct cgggttctcc cgggacttcg tggaggacga cttcgccggt   600
gtggtccggg acgacgtgac cctgttcatc agcgcggtcc aggaccaggt ggtgccggac   660
aacaccctgg cctgggtgtg ggtgcgcggc ctggacgagc tgtacgccga gtggtcggag   720
gtcgtgtcca cgaacttccg ggacgcctcc gggccggcca tgaccgagat cggcgagcag   780
ccgtgggggc gggagttcgc cctgcgcgac ccggccggca actgcgtgca cttcgtggcc   840
gaggagcagg actga                                                  855

<210> SEQ ID NO 20
<211> LENGTH: 1086
<212> TYPE: DNA
<213> ORGANISM: Artificial Sequence
<220> FEATURE:
<223> OTHER INFORMATION: G418

<400> SEQUENCE: 20
tacagagctt tatatcacct tactgaacgc tagagtagac ccaattcccg gctcacacca    60
cccttacatg cagagctaac caataaggta attaattaac actatatagc tcgtggtgaa   120
cactggcccg gagtagtcat acgtgtaggt ttttggcgtg atgaaaatca ggtggcgcac   180
gacttttcgt aaagttcggg agggagtgct gcaaacggca tataaggacc agttttttctc   240 gcacattatc aattgctctt tagtacaaag ataatataga aaccatatga ttgaacaaga   300
tggattgcac gcaggttctc cggccgcttg ggtggagagg ctattcggct atgactgggc   360
acaacagaca atcggctgct ctgatgccgc cgtgttccgg ctgtcagcgc aggggcgccc   420
ggttcttttt gtcaagaccg acctgtccgg tgccctgaat gaactgcagg acgaggcagc   480
gcggctatcg tggctggcca cgacgggcgt tccttgcgca gctgtgctcg acgttgtcac   540
tgaagcggga agggactggc tgctattggg cgaagtgccg gggcaggatc tcctgtcatc   600
```

| | |
|---|---|
| tcaccttgct cctgccgaga aagtatccat catggctgat gcaatgcggc ggctgcatac | 660 |
| gcttgatccg gctacctgcc cattcgacca ccaagcgaaa catcgcatcg agcgagcacg | 720 |
| tactcggatg aagccggtc ttgtcgatca ggatgatctg gacgaagagc atcaggggct | 780 |
| cgcgccagcc gaactgttcg ccaggctcaa ggcgcgcatg cccgacggcg aggatctcgt | 840 |
| cgtgacccat ggcgatgcct gcttgccgaa tatcatggtg aaaatggcc gcttttctgg | 900 |
| attcatcgac tgtggccggc tgggtgtggc ggaccgctat caggacatag cgttggctac | 960 |
| ccgtgatatt gctgaagagc ttggcggcga atgggctgac cgcttcctcg tgctttacgg | 1020 |
| tatcgccgct cccgattcgc agcgcatcgc cttctatcgc cttcttgacg agttcttctg | 1080 |
| agcggg | 1086 |

<210> SEQ ID NO 21
<211> LENGTH: 1056
<212> TYPE: DNA
<213> ORGANISM: Artificial Sequence
<220> FEATURE:
<223> OTHER INFORMATION: Anti b-gal scFv gene

<400> SEQUENCE: 21

| | |
|---|---|
| atgagatttc cttcaattt tactgcagtt ttattcgcag catcctccgc attagctgct | 60 |
| ccagtcaaca ctacaacaga agatgaaacg gcacaaattc cggctgaagc tgtcatcggt | 120 |
| tactcagatt tagaagggga tttcgatgtt gctgttttgc cattttccaa cagcacaaat | 180 |
| aacgggttat tgtttataaa tactactatt gccagcattg ctgctaaaga agaaggggta | 240 |
| tctctcgaga aaagagaggc tgaagcttac gtagaattcg ctcaggttca attgcaagaa | 300 |
| tccggtccag gtttggttaa gccatctgag actttgtcct tgacttgtac tgtttccggt | 360 |
| ggttccattt cctcttacca ctggtcctgg attagacagc caccaggtaa aggtttggag | 420 |
| tggatcggtt acatctacta ctccggttcc actaactaca acccatcctt gaagaacaga | 480 |
| gttactatct ccgttgacac ttccaagaac cagttctcct tgaacttgag atccgttact | 540 |
| gctgctgaca ctgctgttta ctactgtgct agaggtactt acggtccagc tggtgatgct | 600 |
| ttcgatattt ggggtcaggg tactactgtt acagtttcct ctggtggtgg tggatcaggt | 660 |
| ggtggtggtt ctggtggtgg tggatctgat attcaaatga ctcagtcccc atccactttg | 720 |
| tccgcttcta ttggtgatag agttacaatt acttgtagag cttccgaggg tatctaccat | 780 |
| tggttggctt ggtatcaaca gaagccaggt aaggctccaa agttgttgat ctacaaggct | 840 |
| tcctcttttgg cttctggtgc tccatctaga ttttctggtt ccggttctgg tactgacttt | 900 |
| actttgacta tctcctcctt gcaacctgac gacttcgcta cttactattg tcagcagtac | 960 |
| tccaactacc cattgacttt cggtggtggt actaagttgg agatcaagag agctgctgct | 1020 |
| ggtggtggtg gttcacatca tcatcatcat cactag | 1056 |

<210> SEQ ID NO 22
<211> LENGTH: 36
<212> TYPE: DNA
<213> ORGANISM: Artificial Sequence
<220> FEATURE:
<223> OTHER INFORMATION: gene fragment with multiple cloning sites of
    HindIII-BamHI-BglII-XbaI-EcoRI

<400> SEQUENCE: 22

| | |
|---|---|
| tttaagcttg gatccagatc ttctagagaa ttcaaa | 36 |

<210> SEQ ID NO 23

```
<211> LENGTH: 35
<212> TYPE: DNA
<213> ORGANISM: Artificial Sequence
<220> FEATURE:
<223> OTHER INFORMATION: primer13

<400> SEQUENCE: 23
ttaagatcta tgagatttcc ttcaattttt actgc                                35

<210> SEQ ID NO 24
<211> LENGTH: 36
<212> TYPE: DNA
<213> ORGANISM: Artificial Sequence
<220> FEATURE:
<223> OTHER INFORMATION: primer14

<400> SEQUENCE: 24
ttaagatctc tagtgatgat gatgatgatg tgaacc                               36

<210> SEQ ID NO 25
<211> LENGTH: 36
<212> TYPE: DNA
<213> ORGANISM: Artificial Sequence
<220> FEATURE:
<223> OTHER INFORMATION: gene fragment with multiple cloning sites of
      HindIII-BamHI-SpeI-XbaI-EcoRI

<400> SEQUENCE: 25
tttaagcttg gatccactag ttctagagaa ttcaaa                               36

<210> SEQ ID NO 26
<211> LENGTH: 33
<212> TYPE: DNA
<213> ORGANISM: Artificial Sequence
<220> FEATURE:
<223> OTHER INFORMATION: primer15

<400> SEQUENCE: 26
ttagaattcc ccacacacca tagcttcaaa atg                                  33

<210> SEQ ID NO 27
<211> LENGTH: 31
<212> TYPE: DNA
<213> ORGANISM: Artificial Sequence
<220> FEATURE:
<223> OTHER INFORMATION: primer16

<400> SEQUENCE: 27
ttagaattct cagtcctgct cctcggccac g                                    31

<210> SEQ ID NO 28
<211> LENGTH: 28
<212> TYPE: DNA
<213> ORGANISM: Artificial Sequence
<220> FEATURE:
<223> OTHER INFORMATION: primer17

<400> SEQUENCE: 28
tgtgttttga tagttgttca attgattg                                        28

<210> SEQ ID NO 29
<211> LENGTH: 30
<212> TYPE: DNA
<213> ORGANISM: Artificial Sequence
<220> FEATURE:
<223> OTHER INFORMATION: primer18
```

<400> SEQUENCE: 29
gacaataaga agaaaaaaaa agaaaagcgg          30

<210> SEQ ID NO 30
<211> LENGTH: 888
<212> TYPE: PRT
<213> ORGANISM: Komagataella pastoris

<400> SEQUENCE: 30

```
Met Ser Thr Ala Ala Pro Ile Lys Glu Glu Ser Gln Phe Ala His Leu
1               5                   10                  15

Thr Leu Met Asn Lys Asp Ile Pro Ser Asn Ala Lys Gln Ala Lys Ser
            20                  25                  30

Lys Val Ser Ala Ala Pro Ala Lys Thr Gly Ser Lys Ser Ala Gly Gly
        35                  40                  45

Ser Gly Asn Asn Asn Ala Ala Pro Val Lys Lys Arg Val Arg Thr Gly
    50                  55                  60

Cys Leu Thr Cys Arg Lys Lys His Lys Lys Cys Asp Glu Asn Arg Asn
65                  70                  75                  80

Pro Lys Cys Asp Phe Cys Thr Leu Lys Gly Leu Glu Cys Val Trp Pro
                85                  90                  95

Glu Asn Asn Lys Lys Asn Ile Phe Val Asn Asn Ser Met Lys Asp Phe
            100                 105                 110

Leu Gly Lys Lys Thr Val Asp Gly Ala Asp Ser Leu Asn Leu Ala Val
        115                 120                 125

Asn Leu Gln Gln Gln Ser Ser Asn Thr Ile Ala Asn Gln Ser Leu
    130                 135                 140

Ser Ser Ile Gly Leu Glu Ser Phe Gly Tyr Gly Ser Gly Ile Lys Asn
145                 150                 155                 160

Glu Phe Asn Phe Gln Asp Leu Ile Gly Ser Asn Ser Gly Ser Ser Asp
                165                 170                 175

Pro Thr Phe Ser Val Asp Ala Asp Glu Ala Gln Lys Leu Asp Ile Ser
            180                 185                 190

Asn Lys Asn Ser Arg Lys Arg Gln Lys Leu Gly Leu Leu Pro Val Ser
        195                 200                 205

Asn Ala Thr Ser His Leu Asn Gly Phe Asn Gly Met Ser Asn Gly Lys
    210                 215                 220

Ser His Ser Phe Ser Ser Pro Ser Gly Thr Asn Asp Asp Glu Leu Ser
225                 230                 235                 240

Gly Leu Met Phe Asn Ser Pro Ser Phe Asn Pro Leu Thr Val Asn Asp
                245                 250                 255

Ser Thr Asn Asn Ser Asn His Asn Ile Gly Leu Ser Pro Met Ser Cys
            260                 265                 270

Leu Phe Ser Thr Val Gln Glu Ala Ser Gln Lys Lys His Gly Asn Ser
        275                 280                 285

Ser Arg His Phe Ser Tyr Pro Ser Gly Pro Glu Asp Leu Trp Phe Asn
    290                 295                 300

Glu Phe Gln Lys Gln Ala Leu Thr Ala Asn Gly Glu Asn Ala Val Gln
305                 310                 315                 320

Gln Gly Asp Asp Ala Ser Lys Asn Asn Thr Ala Ile Pro Lys Asp Gln
                325                 330                 335

Ser Ser Asn Ser Ser Ile Phe Ser Arg Ser Ser Ala Ala Ser Ser
            340                 345                 350

Asn Ser Gly Asp Asp Ile Gly Arg Met Gly Pro Phe Ser Lys Gly Pro
```

```
                355                 360                 365
Glu Ile Glu Phe Asn Tyr Asp Ser Phe Leu Glu Ser Leu Lys Ala Glu
    370                 375                 380

Ser Pro Ser Ser Lys Tyr Asn Leu Pro Glu Thr Leu Lys Glu Tyr
385                 390                 395                 400

Met Thr Leu Ser Ser His Leu Asn Ser Gln His Ser Asp Thr Leu
                405                 410                 415

Ala Asn Gly Thr Asn Gly Asn Tyr Ser Ser Thr Val Ser Asn Asn Leu
            420                 425                 430

Ser Leu Ser Leu Asn Ser Phe Ser Phe Ser Asp Lys Phe Ser Leu Ser
        435                 440                 445

Pro Pro Thr Ile Thr Asp Ala Glu Lys Phe Ser Leu Met Arg Asn Phe
    450                 455                 460

Ile Asp Asn Ile Ser Pro Trp Phe Asp Thr Phe Asp Asn Thr Lys Gln
465                 470                 475                 480

Phe Gly Thr Lys Ile Pro Val Leu Ala Lys Lys Cys Ser Ser Leu Tyr
                485                 490                 495

Tyr Ala Ile Leu Ala Ile Ser Ser Arg Gln Arg Glu Arg Ile Lys Lys
            500                 505                 510

Glu His Asn Glu Lys Thr Leu Gln Cys Tyr Gln Tyr Ser Leu Gln Gln
        515                 520                 525

Leu Ile Pro Thr Val Gln Ser Ser Asn Asn Ile Glu Tyr Ile Ile Thr
    530                 535                 540

Cys Ile Leu Leu Ser Val Phe His Ile Met Ser Ser Glu Pro Ser Thr
545                 550                 555                 560

Gln Arg Asp Ile Ile Val Ser Leu Ala Lys Tyr Ile Gln Ala Cys Asn
                565                 570                 575

Ile Asn Gly Phe Thr Ser Asn Asp Lys Leu Glu Lys Ser Ile Phe Trp
            580                 585                 590

Asn Tyr Val Asn Leu Asp Leu Ala Thr Cys Ala Ile Gly Glu Glu Ser
        595                 600                 605

Met Val Ile Pro Phe Ser Tyr Trp Val Lys Glu Thr Thr Asp Tyr Lys
    610                 615                 620

Thr Ile Gln Asp Val Lys Pro Phe Phe Thr Lys Lys Thr Ser Thr Thr
625                 630                 635                 640

Thr Asp Asp Asp Leu Asp Asp Met Tyr Ala Ile Tyr Met Leu Tyr Ile
                645                 650                 655

Ser Gly Arg Ile Ile Asn Leu Leu Asn Cys Arg Asp Ala Lys Leu Asn
            660                 665                 670

Phe Glu Pro Lys Trp Glu Phe Leu Trp Asn Glu Leu Asn Glu Trp Glu
        675                 680                 685

Leu Asn Lys Pro Leu Thr Phe Gln Ser Ile Val Gln Phe Lys Ala Asn
    690                 695                 700

Asp Glu Ser Gln Gly Gly Ser Thr Phe Pro Thr Val Leu Phe Ser Asn
705                 710                 715                 720

Ser Arg Ser Cys Tyr Ser Asn Gln Leu Tyr His Met Ser Tyr Ile Ile
                725                 730                 735

Leu Val Gln Asn Lys Pro Arg Leu Tyr Lys Ile Pro Phe Thr Thr Val
            740                 745                 750

Ser Ala Ser Met Ser Pro Ser Asp Asn Lys Ala Gly Met Ser Ala
        755                 760                 765

Ser Ser Thr Pro Ala Ser Asp His His Ala Ser Gly Asp His Leu Ser
    770                 775                 780
```

Pro Arg Ser Val Glu Pro Ser Leu Ser Thr Thr Leu Ser Pro Pro
785                 790                 795                 800

Asn Ala Asn Gly Ala Gly Asn Lys Phe Arg Ser Thr Leu Trp His Ala
            805                 810                 815

Lys Gln Ile Cys Gly Ile Ser Ile Asn Asn Asn His Asn Ser Asn Leu
            820                 825                 830

Ala Ala Lys Val Asn Ser Leu Gln Pro Leu Trp His Ala Gly Lys Leu
            835                 840                 845

Ile Ser Ser Lys Ser Glu His Thr Gln Leu Leu Lys Leu Leu Asn Asn
            850                 855                 860

Leu Glu Cys Ala Thr Gly Trp Pro Met Asn Trp Lys Gly Lys Glu Leu
865                 870                 875                 880

Ile Asp Tyr Trp Asn Val Glu Glu
                885

<210> SEQ ID NO 31
<211> LENGTH: 116
<212> TYPE: DNA
<213> ORGANISM: Artificial Sequence
<220> FEATURE:
<223> OTHER INFORMATION: primer19

<400> SEQUENCE: 31
gggatcgtgt tcttcttctc caattgcaat catatttctg actctttcta gttcagatta      60
attcctttac acttgctttt ttcccttacc tttatcctac agagctttat atcacc         116

<210> SEQ ID NO 32
<211> LENGTH: 118
<212> TYPE: DNA
<213> ORGANISM: Artificial Sequence
<220> FEATURE:
<223> OTHER INFORMATION: primer20

<400> SEQUENCE: 32
ccatcgacat cagccaccaa ggcattcctt ttacagcgtc atccagttga atgaagttca      60
caattagatc attaacatca cataaacata cataactacc cgctcagaag aactcgtc      118

<210> SEQ ID NO 33
<211> LENGTH: 501
<212> TYPE: PRT
<213> ORGANISM: Komagataella pastoris

<400> SEQUENCE: 33

Met Thr Phe Ala Pro Pro Leu Glu Phe Glu Ile Asp Leu Pro Asn Gly
1               5                   10                  15

Leu Lys Tyr Thr Gln Pro Leu Gly Leu Phe Ile Asn Asn Glu Phe Val
            20                  25                  30

Glu Gly Val Glu Gly Lys Leu Leu Pro Val Ile Asn Pro Cys Asp Glu
        35                  40                  45

Thr Lys Ile Thr Gln Val Trp Glu Ala Ser Ala Ala Asp Val Asp Arg
    50                  55                  60

Ala Val Asp Ala Ala Glu Asp Ala Phe Asn Asn Ser Val Trp Ala Thr
65                  70                  75                  80

Gln Asp Pro Leu Glu Arg Gly Lys Leu Met Asn Lys Leu Ala Asp Leu
                85                  90                  95

Ile Asp Arg Asp Phe Asn Ile Leu Ala Gly Ile Glu Ser Ile Asp Asn
            100                 105                 110

Gly Lys Ala Tyr Thr Ser Ala Gln Gly Asp Val Thr Leu Ala Val Asn
            115                 120                 125

Tyr Ile Arg Ser Cys Ala Gly Trp Ala Asp Lys Ile Leu Gly Asn Val
130                 135                 140

Val Asp Ser Gly Asn Thr His Leu Asn Leu Val Lys Arg Glu Pro Leu
145                 150                 155                 160

Gly Val Val Gly Gln Ile Ile Pro Trp Asn Phe Pro Leu Leu Met Leu
                165                 170                 175

Ala Trp Lys Leu Gly Pro Ala Leu Ala Thr Gly Asn Thr Val Val Leu
            180                 185                 190

Lys Thr Ala Glu Ser Thr Pro Leu Ser Gly Leu Tyr Val Ala Lys Leu
        195                 200                 205

Ile Lys Glu Ala Gly Phe Pro Pro Gly Val Val Asn Ile Leu Ser Gly
210                 215                 220

Phe Gly Asn Pro Ala Gly Ala Ala Ile Ala Ala His Pro Arg Ile Lys
225                 230                 235                 240

Lys Ile Ala Phe Thr Gly Ser Thr Ala Thr Gly Arg Lys Ile Met Glu
                245                 250                 255

Ala Ala Ala Lys Ser Asn Leu Lys Lys Val Thr Leu Glu Leu Gly Gly
            260                 265                 270

Lys Ser Pro Asn Ile Val Phe Glu Asp Ala Asp Ile Gln Lys Thr Ile
        275                 280                 285

His Asn Ile Ile Leu Gly Ile Phe Phe Asn Ser Gly Glu Val Cys Cys
    290                 295                 300

Ala Gly Ser Arg Val Tyr Ile Gln Asp Thr Val Tyr Glu Glu Val Leu
305                 310                 315                 320

Glu Ala Phe Lys Lys Glu Thr Asp Asn Val Lys Val Gly Gly Pro Phe
                325                 330                 335

Glu Glu Gly Val Phe Gln Gly Pro Gln Thr Ser Glu Leu Gln Leu Asn
            340                 345                 350

Arg Ile Leu Ser Tyr Ile Lys His Gly Lys Asp Glu Gly Ala Arg Val
        355                 360                 365

Ile Thr Gly Gly Ser Arg Tyr Arg Asn Arg Gly Tyr Tyr Ile Lys Pro
370                 375                 380

Thr Ile Phe Ala Asp Val Thr Glu Asp Met Lys Ile Val Lys Glu Glu
385                 390                 395                 400

Ile Phe Gly Pro Val Val Thr Ile Thr Lys Phe Ser Thr Val Asp Glu
                405                 410                 415

Val Val Gly Tyr Ala Asn Asn Thr Asn Tyr Gly Leu Ala Ala Gly Ile
            420                 425                 430

His Thr Asn Asn Leu Asn Lys Ala Ile Asp Val Ala Ser Arg Ile Lys
        435                 440                 445

Ala Gly Val Val Trp Ile Asn Thr Tyr Asn Asp Phe His His Met Val
450                 455                 460

Pro Phe Gly Gly Tyr Gly Glu Ser Gly Ile Gly Arg Glu Leu Gly Ala
465                 470                 475                 480

Glu Ala Leu Asp Asn Tyr Thr Gln Ala Lys Ala Ile Arg Ile Ala Tyr
                485                 490                 495

Thr Pro Glu His Lys
            500

<210> SEQ ID NO 34
<211> LENGTH: 1506
<212> TYPE: DNA

<213> ORGANISM: Komagataella pastoris

<400> SEQUENCE: 34

```
atgacatttg ctcctcccctt agaattcgag attgaccttc ctaacggatt gaagtacact    60
caaccattgg gactcttcat caacaatgag tttgttgaag gtgtagaggg aaagctctta   120
ccagtgatca atccttgtga tgagactaaa ataacccaag tttgggaagc ttctgcagcg   180
gatgttgacc gtgctgttga tgccgctgaa gatgctttca caactccgt atgggctact   240
caggacccat tagagagggg aaagctgatg aacaaattgg cagaccttat cgatcgtgac   300
ttcaacatct ggctggtat cgaatccatc gacaatggta aggcctatac ctctgcccag   360
ggtgatgtta ctcttgctgt caactacatc agatcctgtg ctggatgggc cgacaagatt   420
ttgggaaacg ttgttgattc cggaaacacc caccttaact tggttaaaag agagccattg   480
ggtgttgtgg acaaattat cccatggaac tttcctctcc tgatgttggc ttggaagttg   540
ggacctgcgc tggccacagg taacactgtt gttttgaaga ctgccgagtc tacccctctg   600
tcgggtttat acgttgccaa attgatcaag gaggccggtt ccccacctgg tgtggttaac   660
attctcagtg gtttcggtaa cccagctgga gctgccatcg ctgctcatcc agaatcaag   720
aagattgctt tcaccggatc cactgcaaca ggccgtaaga tcatggaagc agccgctaaa   780
tctaacctga aaaagtcac tttggaacta ggtggtaaat ctccaaacat tgtgtttgaa   840
gatgctgata tccagaagac tatccataac attattttgg aatcttctt caattctggt   900
gaagtctgtt gtgcaggttc cagagtctac attcaagaca ctgtgtatga agaagtgctt   960
gaagccttca agaaggagac tgataacgtt aaggttggtg accattcga agaaggtgtc  1020
ttccaagggc ctcagaccctc tgagttgcaa cttaacagaa tccttagtta catcaaacac  1080
ggtaaggatg aaggtgctcg tgtaattacc ggtggttcaa gataccgtaa ccagaggttac  1140
tacattaagc ccacaatttt tgctgacgtt actgaagaca tgaagattgt caaggaggag  1200
attttttggtc ctgtggttac tatcactaag ttctctaccg tggatgaggt tgttggatat  1260
gccaacaaca ccaactatgg tctagctgct ggtattcaca caaacaactt gaacaaagcc  1320
attgatgttg ccagtagaat caaggcgggt gtcgtttgga ttaacaccta caacgatttc  1380
caccacatgg ttcctttcgg aggttatgga gaatctggta ttggcagaga cttggtgct  1440
gaggctttgg ataactacac tcaagccaag gctatcagaa ttgcttacac tcctgaacat  1500
aagtag                                                              1506
```

<210> SEQ ID NO 35
<211> LENGTH: 117
<212> TYPE: DNA
<213> ORGANISM: Artificial Sequence
<220> FEATURE:
<223> OTHER INFORMATION: primer21

<400> SEQUENCE: 35

```
accactcctt gaaagttggt cttatcgaag caggtgagaa caacctcaac aacccatggg    60
tctaccttcc aggtatttac ccaagaaaca tgacccacac accatagctt caaaatg     117
```

<210> SEQ ID NO 36
<211> LENGTH: 116
<212> TYPE: DNA
<213> ORGANISM: Artificial Sequence
<220> FEATURE:
<223> OTHER INFORMATION: primer22

<400> SEQUENCE: 36

```
ggcagtcttt tcaccgatca aaagagcggt ggtgtaggtg ttacaaccaa cattgtctgg    60
gcacacggac aagtcaccaa ccttcaagcc cttgtcagtc ctgctcctcg gccacg       116

<210> SEQ ID NO 37
<211> LENGTH: 1992
<212> TYPE: DNA
<213> ORGANISM: Komagataella pastoris

<400> SEQUENCE: 37
atggctatcc ccgaagagtt tgatatccta gttctaggtg gtggatccag tggatcctgt    60
attgccggaa gattggcaaa cttgaccac tccttgaaag ttggtcttat cgaagcaggt   120
gagaacaacc tcaacaaccc atgggtctac cttccaggta tttacccaag aaacatgaag   180
ttggactcca agactgcttc cttctacact tctaacccat ctcctcactt gaatggtaga   240
agagccattg ttccatgtgc taacgtcttg ggtggtggtt cttctatcaa cttcatgatg   300
tacaccagag ttctgcttc tgattacgat gacttccaag ccgagggctg aaaaccaag    360 gacttgcttc cattgatgaa aaagactgag acctaccaaa gagcttgcaa caccctgac   420 attcacggtt tcgaaggtcc aatcaaggtt tctttcggta actacaccta cccagtttgc   480
caggacttct tgagggcttc tgagtcccaa ggtattccat acgttgacga cttggaagac   540
ttggttactg ctcacggtgc tgaacactgg ttgaagtgga tcaacagaga cactggtcgt   600
cgttccgact ctgctcatgc atttgtccac tctactatga aaaccacga caacttgtac   660 ttgatctgta acacgaaggt cgacaaaatt attgtcgaag acggaagagc tgctgctgtt   720
agaaccgttc caagcaagcc tttgaaccca agaagccaa gtcacaagat ctaccgtgct   780
agaaagcaaa tcgttttgtc ttgtggtacc atctcctctc cattggtttt gcaaagatcc   840
ggttttggtg acccaatcaa gttgagagcc gctggtgtta agcctttggt caacttgcca   900
ggtgtcggaa gaacttcca agaccactac tgtttcttca gtccttacag aatcaagcct   960
cagtacgagt ctttcgatga cttcgtccgt ggtgatgctg agattcaaaa gagagtcttt  1020
gaccaatggt acgccaatgg tactggtcct cttgccacta cggtatcga agctggtgtc  1080 aagatcagac aacaccaga agaactctct caaatggacg aatccttcca ggagggttac  1140
agagaatact cgaagacaa gccagacaag ccagttatgc actactccat cattgctggt  1200
ttcttcggtg accacaccaa gattcctcct ggaaagtaca tgactatgtt ccacttcttg  1260
gaatacccat tctccagagg ttccattcac attacctccc cagacccata cgcagctcca  1320
gacttcgacc aggtttcat gaacgatgaa agagacatgg ctcctatggt ttgggcttac  1380
aagaagtcta gagaaaccgc tagaagaatg gaccactttg ccggtgaggt cacttctcac  1440
caccctctgt tcccatactc atccgaggcc agagccttgg aaatggattt ggagacctct  1500
aatgcctacg gtggaccttt gaacttgtct gctggtcttg ctcacggttc ttggactcaa  1560
cctttgaaga gccaactgc aaagaacgaa ggccacgtta cttcgaacca ggtcgagctt  1620
catccagaca tcgagtacga tgaggaggat gacaaggcca ttgagaacta cattcgtgag  1680
cacactgaga ccacatggca ctgtctggga acctgttcca tcggtccaag agaaggttcc  1740
aagatcgtca atggggtgg tgttttggac cacagatcca acgttacgg agtcaagggc  1800 ttgaaggttg gtgacttgtc cgtgtgccca gacaatgttg ttgtaacac ctacaccacc  1860 gctcttttga tcggtgaaaa gactgccact ttggttggag aagatttagg atactctggt  1920
gaggccttag acatgactgt tcctcagttc aagttgggca cttacgagaa gaccggtctt  1980
```

<210> SEQ ID NO 38
<211> LENGTH: 118
<212> TYPE: DNA
<213> ORGANISM: Artificial Sequence
<220> FEATURE:
<223> OTHER INFORMATION: primer23

<400> SEQUENCE: 38

```
gccttacctg atcgcaatca ggatttcact actcatataa atacatcgct caaagctcca    60
actttgcttg ttcatacaat tcttgatatt cacacccaca caccatagct tcaaaatg     118
```

<210> SEQ ID NO 39
<211> LENGTH: 116
<212> TYPE: DNA
<213> ORGANISM: Artificial Sequence
<220> FEATURE:
<223> OTHER INFORMATION: primer24

<400> SEQUENCE: 39

```
tatatacgta tacatacata tatatacata ggtctataaa cgtcctagct gagatcgggc    60
cttacataac tcattcattc atcatacgtc gtactcagtc ctgctcctcg gccacg       116
```

<210> SEQ ID NO 40
<211> LENGTH: 1140
<212> TYPE: DNA
<213> ORGANISM: Komagataella pastoris

<400> SEQUENCE: 40

```
atgtctaccg aaggtcaaat catcaaatgt aaggcagctg ttgcctggga ggcaggaaag    60
gatctctcta ttgaggagat tgaggttctt cctccaagag cccatgaagt tagagtgaaa   120
gtggaattca ctggtgtatg ccacactgat gcttacacgc tttctggtgc agatgcagag   180
ggaagtttcc ctgttgtgtt cggccatgaa ggtgctggtg ttgtcgagtc agttggagaa   240
ggtgttgagt ccgtgaaggt tggggattct gtagtgcttc tgtacactcc tgagtgcaga   300
gagtgcaagt tctgtctgtc tggtaagacg aacctctgtg gtaaaatcag agccacccag   360
ggtaaaggtt tgttaccaga cgggacttct cgtttccgtt gtaagggcaa ggatttgttt   420
cactatatgg gatgttcttc cttttctcaa tacactgtgg tggctgacat ctcagtggtt   480
aaagtccaag acgaagctcc taaggacaag acatgtctgt gggttgtgg tgttaccaca   540
gggtacggtg ctgctatcaa cactgctaag atctctaagg gtgacaagat cggtgtgttt   600
ggtgctggat gtattggatt atctgtcatc caaggtgcag tttccaaagg tgcaagcgag   660
attattgtaa ttgacatcaa tgattcaaag aaggcatggg cggaccaatt tggtgcaact   720
aagtttgtca atcctacaac cttaccagaa ggtaccaata ttgttgacta cttgattgat   780
atcactgacg gaggctttga ctataccttc gactgtaccg gtaatgttca agtaatgaga   840
aatgcacttg aatcttgcca agggttgg ggtgagtcga tcatcatcgg tgtcgctgct   900
gctggtaaag aaatctctac ccgtcctttc cagttggtta ctggcagagt ctggagagga   960
tgcgcctttg gaggtatcaa gggacgtact caaatgccat ctttggttca ggactatctt   1020
gatggtaaga ttaaagttga cgagtttatc acacacagac atgacctgga caacatcaac  1080
aaagcatttc atgacatgca tgctggaaac tgtattcgtg ctgtgattac tatgcactaa  1140
```

<210> SEQ ID NO 41
<211> LENGTH: 104

```
<212> TYPE: DNA
<213> ORGANISM: Artificial Sequence
<220> FEATURE:
<223> OTHER INFORMATION: primer25

<400> SEQUENCE: 41
tttgaaacta ttttcagtat cttgattcgt ttacttacaa acaactattg ttgattttat   60
ctggagaata atcgaacaaa cccacacacc atagcttcaa aatg                  104

<210> SEQ ID NO 42
<211> LENGTH: 100
<212> TYPE: DNA
<213> ORGANISM: Artificial Sequence
<220> FEATURE:
<223> OTHER INFORMATION: primer26

<400> SEQUENCE: 42
ttaattaaac aaaacaaaac gtactagcat tactgtcata tataagggct cctaactaaa   60
actgtaaaga cttcccgttc agtcctgctc ctcggccacg                       100

<210> SEQ ID NO 43
<211> LENGTH: 2124
<212> TYPE: DNA
<213> ORGANISM: Komagataella pastoris

<400> SEQUENCE: 43
atggctagaa ttcccaaagc agtttcttac aatgatgaca tccatgactt ggtcatcaaa   60
accttccgtt gttacgttct cgacttagtc gaacagtatg gtggtggtca ccctggttct  120
gccatgggta tggtcgccat tggtatcgct ctgtggaagt accagatgaa gtacgctcca  180
aatgatccag actacttcaa cagagatcgt tttgtcttgt caaacggtca cgtctgtttg  240
ttccaatact tgttccagca cttaactggt ttgaaggaga tgactgtcaa gcaacttcaa  300
tcttaccact cttccgatta tcactcattg actcctggac accctgaaat tgagaaccct  360
gctgttgagg ttaccactgg tcccctggga caaggtatct ctaacgctgt cggtatggcc  420
attggttcaa agaacctggc cgctacttac aacagacctg gcttccctgt cgttgacaac  480
actatctatg ctattgttgg tgatgcttgt ttgcaagagg gacctgcttt ggaatcgatt  540
tccttagccg tcacttggc cttggacaac cttattgtga ctacgacaa caaccaggtt  600
tgttgtgatg gttccgtcga tgttaacaac accgaagaca tctccgcaaa gttcagagct  660
cagaactgga atgttatcga cattgtagac ggttctagag atgtcgctac cattgtcaag  720
gctatcgatt gggccaaggc tgagactgag agaccaactc tgatcaacgt tagaactgaa  780
attggacagg attctgcttt cggtaaccac cacgctgctc acggttctgc tctaggtgag  840
gaaggtatcc gggagttgaa gactaagtac ggttttaacc ctgcccaaaa gttctggttc  900
cctaaagaag tatacgactt ctttgctgag aaaccagcta aggtgacga gttagtaaag  960
aactggaaaa agttagttga tagctatgtc aaagagtacc ctcgtgaggg acaagagttc 1020
ctttctcgtg ttagaggtga gcttccaaag aactggagaa cttacattcc tcaagacaag 1080
cctaccgaac caaccgccac cagaacctct gctagagaaa ttgttagggc ccttggaaag 1140
aaccttcctc aagttattgc cggttccggt gactatctg tctcaattct ttgaactgg  1200
gacggagtga agtacttctt caaccctaag ttacagactt tctgtggatt aggtggtgac 1260
tactctggta gatatattga gtttggtatc agagaacact ctatgtgtgc tattgccaac 1320
ggtttggctg catacaacaa gggtacttc ttgcctatta cctctacctt ctacatgttc 1380
```

```
tacctgtatg cagcacctgc cttgcgtatg gctgctcttc aagagttgaa agcgattcac    1440
attgctacac acgactctat tggagctggt gaagatggtc aacccacca gcctattgct    1500 ttgtcttcat tattcagagc tatgcccaac ttctactaca tgagaccagc cgatgctacc    1560
gaagttgcag ctctgtttga agtggctgtt gagcttgaac actccacatt gctttctctg    1620
tccagacacg aggttgacca ataccaggt aagacttctg cccaaggagc caaaagaggt    1680
ggttacgttg ttgaagactg cgaaggaaag ccagatgtgc aactgatcgg aactggttcc    1740
gagttggaat tcgctattaa gactgctcgt ttgctaagac aacagaaggg atggaaggtc    1800
agagttctgt cattcccatg tcagagattg tttgacgagc agtctattac ttacagacgt    1860
tccgtcctta gaagaggaga agttccaact gtcgttgttg aggcctatgt cgcatacgga    1920
tgggagagat acgccactgc tggttacacc atgaacacct tcggtaagtc tcttcctgtt    1980
gaggatgtct acaaatactt cggatacact cctgagaaga ttggtgagag agtggttcaa    2040
tatgtcaact ctatcaaggc tagtcctcaa atcctttacg aattccacga cttgaaggga    2100
aaaccaaagc atgacaagtt gtaa                                          2124

<210> SEQ ID NO 44
<211> LENGTH: 99
<212> TYPE: DNA
<213> ORGANISM: Artificial Sequence
<220> FEATURE:
<223> OTHER INFORMATION: primer27

<400> SEQUENCE: 44
taagaccaaa accagttaca acaaattata acccctctaa acactaaagt tcactcttat    60
caaactatca acatcaaaa tacagagctt tatatcacc                           99

<210> SEQ ID NO 45
<211> LENGTH: 98
<212> TYPE: DNA
<213> ORGANISM: Artificial Sequence
<220> FEATURE:
<223> OTHER INFORMATION: primer28

<400> SEQUENCE: 45
actacgatga tcatccataa acaaaaatca aatttaatag acttacacaa ctactaaccc    60
gttagtggcc aaatctaccc cgctcagaag aactcgtc                           98

<210> SEQ ID NO 46
<211> LENGTH: 2124
<212> TYPE: DNA
<213> ORGANISM: Komagataella pastoris

<400> SEQUENCE: 46
atggctagaa ttccaaaagc agtatcgaca caagatgaca ttcatgaatt ggtcatcaaa    60
accttccgtt gttacgttct cgacttagtc gaacagtatg gtggtggtca ccctggttct    120
gccatgggta tggtcgccat tggtatcgct ctgtggaagt accagatgaa gtacgctcca    180
aatgatccag actacttcaa cagagatcgt tttgtcttgt caaacggtca cgtctgtctg    240
ttccaatact tgttccagca cttaactggt tgaaggaga tgactgtcaa gcaacttcaa    300
tcttaccact cttccgatta tcactcattg actcctggac accctgaaat tgagaaccct    360
gctgttgagg ttaccactgg tccctggga caaggtatct ctaacgctgt cggtatggcc    420
attggttcaa agaacctggc cgctacttac aacagacctg gcttcccgtg cgttgacaac    480
actatctatg ctattgttgg tgatgcttgt ttgcaagagg gacctgcttt ggaatcgatt    540
```

-continued

```
tccttagctg gtcacttggc cttggacaac cttattgtga tctacgacaa caaccaggtt      600
tgttgtgatg gttccgtcga tgttaacaac accgaagaca tttctgctaa gtttagagct      660
cagaactgga atgtcattga agtcgagaat ggttctagag atgttgctac ccttgtcaag      720
gccatcgaat gggccaaggc tgagaatgag agaccaactc tgatcaacgt tagaactgaa      780
attggacagg attctgcttt cggtaaccac cacgctgctc acggttctgc tcttggtgag      840
gaaggtatcc gggagttgaa ggccaagtac ggtttcgatg tcgctagaaa gttctggttc      900
ccacaggagg tctatgattt ctttgctgaa aaaccagccg agggtgatca actagttgct      960
aactggaaga aacttttgga tgagtacgtt aagaactatc ctcaagaagg tgaggaatta     1020
aaggcccgta ttagaggtga acttccaaag aactggaaga gtttcattcc acaggacaaa     1080
ccaaccgagc caactgctac cagaacctct gctagagaaa ttgttagatc tctgggacaa     1140
aaccttcctc aggttattgc tggttctggt gacttgtccg tgtccattct tttgaactgg     1200
ggaggagtta agtacttctt caaccctaag ttacaaactt tctgtggatt gggtggtgac     1260
tactctggta gatatattga gtttggtatc agagaacact ctatgtgtgc tattgccaat     1320
ggtttggctg catacaacaa gggtactttc ttgcctatta cctcaacttt ctacatgttc     1380
tacctgtatg cagcacctgc cttgcgtatg gctgcacttc aagagttgaa agcaattcac     1440
attgctacac acgactccat cggagctggt gaagatggtc caacgcacca gcctattgct     1500
ttgtcttcat tattcagagc tatgcccaac ttctactaca ttagaccagc cgatgctacc     1560
gaggttgcag ctctgtttga agtagctgtt gagctcgagc actccacctt gttctctctg     1620
tccagacacg aggttgagca atacccaggt aagacttcgg ctgagggagc caaaagaggt     1680
ggttacgtcg ttgaagactg tgagggtaag ccagacgtcc aattaattgg tgctggttcc     1740
gaattggagt ttgccgtcaa aactgctcgt ttgctaagac aacagaaggg atggaaggtc     1800
agagttctgt cattcccatg tcagagactg tttgaccaac aatccctggc atacagacgt     1860
tctgtcctta gaagaggaga ggttccaact gtcgttgttg aggcctatgt cgcatacgga     1920
tgggagagat acgccactgc tggttacacc atgaacacct ttggtaagtc tcttcctgtt     1980
gaggatgtct acaaatactt cggatacact cctgagaaga ttggtgagaa ggttgctgca     2040
tacgtcaact ctattaaggc tagtcctcaa atcctttacg aattcaccga tttgaaggga     2100
aaaccaaagc acgacaaact ataa                                            2124
```